(12) United States Patent
Allen et al.

(10) Patent No.: US 7,378,447 B2
(45) Date of Patent: May 27, 2008

(54) MUSCARINIC AGONISTS

(75) Inventors: Jennifer Rebecca Allen, Indianapolis, IN (US); Stephen Andrew Hitchcock, New Bury Park, CA (US); William Wilson Turner, Lawai, HI (US); Bin Liu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 295 days.

(21) Appl. No.: 10/546,906

(22) PCT Filed: Mar. 12, 2004

(86) PCT No.: PCT/US2004/005234

§ 371 (c)(1),
(2), (4) Date: Aug. 24, 2005

(87) PCT Pub. No.: WO2004/094363

PCT Pub. Date: Nov. 4, 2004

(65) Prior Publication Data

US 2006/0178438 A1    Aug. 10, 2006

Related U.S. Application Data

(60) Provisional application No. 60/456,911, filed on Mar. 21, 2003.

(51) Int. Cl.
*A01N 37/18* (2006.01)
*A01N 31/165* (2006.01)

(52) U.S. Cl. .................. 514/621; 514/319; 564/147; 564/309; 546/205

(58) Field of Classification Search ................ 514/620, 514/319; 564/147, 309; 546/205
See application file for complete search history.

(56) References Cited

U.S. PATENT DOCUMENTS

| 6,211,364 | B1 * | 4/2001 | Huff et al. .................. 544/106 |
| 6,429,317 | B1 * | 8/2002 | Hollinshead et al. ........ 548/566 |
| 2001/0012848 | A1 * | 8/2001 | Hollinshead et al. ........ 514/319 |

FOREIGN PATENT DOCUMENTS

| WO | WO 97/25983 | 7/1997 |
| WO | WO 98/31660 | 7/1998 |
| WO | WO 99/04778 | 2/1999 |

* cited by examiner

*Primary Examiner*—Yvonne Eyler
*Assistant Examiner*—Chukwuma O Nwaonicha
(74) *Attorney, Agent, or Firm*—R. Craig Tucker; Danica Hostettler

(57) ABSTRACT

The present invention relates to compounds of Formula (I): which are agonists of the M-1 muscarinic receptor (I)

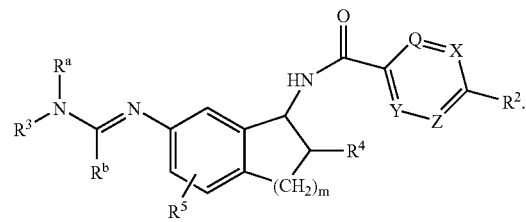

12 Claims, No Drawings

MUSCARINIC AGONISTS

This is the national phase application, under 35 U.S.C. §371, for PCT/US2004/005234 filed on 12 Mar. 2004, which claims the priority of U.S. Provisional Application No. 60/456,911 filed on 21 Mar. 2003.

The present invention relates to the field of pharmaceutical and organic chemistry and provides compounds that are active at the muscarinic receptors.

The compounds of the present invention are muscarinic agonists. More specifically, the compounds of the present invention are selective agonists of the muscarinic M-1 receptor. As such, they are useful for treating a variety of disorders of the central nervous system and other body systems. These disorders include cognitive disorders, ADHD, obesity, Alzheimer's disease, psychoses including schizophrenia, and for alleviation of intraocular pressure such as that found in glaucoma.

Certain indane-like compounds are described as useful for treating conditions associated with malfunctioning of the muscarinic cholinergic system in PCT Publication Nos. WO 97/25983, published 24 Jul. 1997, and WO 99/04778, published 4 Feb. 1999.

The present invention provides compounds of Formula I:

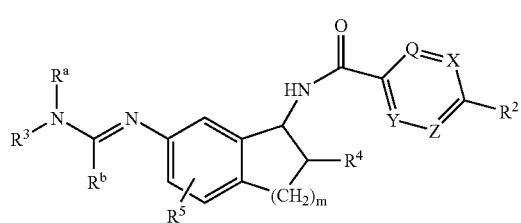

I wherein
- Q, X, Y, and Z are independently selected from the group consisting of $CR^1$ and N, provided that no more than two of Q, X, Y, and Z are N and at least two of Q, X, Y, and Z are CH; or Y is CH, Z is CH, and the moiety "Q=X" represents "S" to form a thiophene ring;
- $R^1$ is independently at each occurrence selected from the group consisting of hydrogen, halogen, $C_1$-$C_4$ alkoxy, and $C_1$-$C_4$ alkyl;
- $R^2$ is selected from the group consisting of halogen; $C_1$-$C_4$ alkoxy; $C_1$-$C_4$ alkyl; $C_3$-$C_8$ cycloalkyl; cyano; trifluoromethyl; pyridinyl optionally substituted with one to two substituents independently selected from the group consisting of halogen, $C_1$-$C_4$ alkoxy, and $C_1$-$C_4$ alkyl; thienyl optionally substituted with one substituent selected from the group consisting of halogen, $C_1$-$C_4$ alkoxy, and $C_1$-$C_4$ alkyl; phenyl optionally substituted with from one to three substituents independently selected from the group consisting of halogen, $C_1$-$C_4$ alkoxy, $C_1$-$C_4$ alkyl, trifluoromethyl, and cyano; and pyrrolyl optionally substituted with one to two substituents independently selected from the group consisting of halogen, $C_1$-$C_4$ alkoxy, and $C_1$-$C_4$ alkyl;
- $R^3$ is a radical of the formula (Z)-(Y)—(X)— wherein
    X is selected from the group consisting of

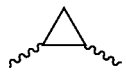

and a straight-chain $C_1$-$C_4$ alkandiyl optionally substituted with methyl, geminal dimethyl, or phenyl;
    Y is selected from the group consisting of O and S; and
    Z is selected from the group consisting of $C_1$-$C_6$ alkyl; $C_3$-$C_8$ cycloalkyl optionally substituted with one to three substituents independently selected from the group consisting of halogen, $C_1$-$C_4$ alkoxy, $C_1$-$C_4$ alkyl, trifluoromethyl, cyano, and nitro; phenyl optionally substituted with one to three substituents independently selected from the group consisting of halogen, $C_1$-$C_4$ alkoxy, $C_1$-$C_4$ alkyl, trifluoromethyl, cyano, and nitro; naphthyl optionally substituted with one to three substituents independently selected from the group consisting of halogen, $C_1$-$C_4$ alkoxy, $C_1$-$C_4$ alkyl, trifluoromethyl, cyano, and nitro; heteroaryl optionally substituted with one or two substituents independently selected from the group consisting of halogen, $C_1$-$C_4$ alkoxy, and $C_1$-$C_4$ alkyl; and heterocycle optionally substituted with one or two substituents independently selected from the group consisting of halogen, $C_1$-$C_4$ alkoxy, and $C_1$-$C_4$ alkyl;
- $R^a$ is selected from the group consisting of hydrogen and methyl;
- or $R^3$ and $R^a$ are taken together with the nitrogen with which they are attached to form a heterocycle optionally substituted with one or two substituents independently selected from the group consisting of halogen, $C_1$-$C_4$ alkoxy, and $C_1$-$C_4$ alkyl;
- $R^4$ is selected from the group consisting of hydrogen, hydroxy, and fluoro;
- $R^5$ is selected from the group consisting of hydrogen, halogen, $C_1$-$C_4$ alkoxy, and $C_1$-$C_4$ alkyl;
- $R^b$ is selected from the group consisting of hydrogen, methyl, and ethyl; and
- m is one or two;
- or pharmaceutically acceptable addition salts thereof.

The present invention also provides pharmaceutical compositions, comprising a compound of Formula I and a pharmaceutically acceptable diluent.

Because the compounds of Formula I are agonists of the M-1 muscarinic receptor, the compounds of Formula I are useful for the treatment of a variety of disorders associated with muscarinic receptors, including: cognitive disorders (including age-related cognitive disorder, mild cognitive impairment, cognitive impairment associated with schizophrenia, and chemotherapy-induced cognitive impairment), ADHD, mood disorders (including depression, mania, bipolar disorders), psychosis (in particular schizophrenia), dementia (including Alzheimer's disease, AIDS-induced dementia, vascular dementia, and dementia lacking distinctive histology), Parkinson's disease, and Huntington's Chorea. Also, the present compounds are useful for treating chronic colitis, including Crohn's disease. Additionally, the present compounds are useful for the treatment of pain (including acute pain and chronic pain), xerostomia (dry mouth), Lewy body disease (including diffuse Lewy body disease), aphasia (including primary aphasia and primary aphasia syndromes), and hypotensive syndromes.

In another embodiment the present invention provides methods of treating disorders associated with muscarinic receptors, comprising: administering to a patient in need thereof an effective amount of a compound of Formula I. That is, the present invention provides for the use of a compound of Formula I or a pharmaceutical composition thereof for the manufacture of a medicament for the treatment of disorders associated with muscarinic receptors. The present invention also provides a compound of Formula I for use in therapy.

As used herein, the following terms have the meanings indicated:

The term "halo" or "halogen" refers to a chloro, fluoro, bromo or iodo atom.

The term "$C_1$-$C_4$ alkyl" refers to a straight or branched alkyl chain having from one to four carbon atoms, examples of which include methyl, ethyl, n-propyl, iso-propyl, n-butyl, sec-butyl, iso-butyl, and t-butyl. The term "$C_1$-$C_4$ alkandiyl" refers to a straight- or branched-chain alkandiyl having from one to four carbon atoms in total, examples of which include methylene, ethylene, tetramethylene, 1-methylpropan-1,3-diyl, 2-methylpropan-1,3-diyl, and butan-2,3-diyl. The term "$C_3$-$C_8$ cycloalkyl" refers to cyclopropyl, cyclobutyl, cyclopentyl, cyclohexyl, cycloheptyl, and cyclooctyl.

The term "$C_1$-$C_4$ alkoxy" refers to a straight or branched alkyl chain having from one to four carbon atoms attached to an oxygen atom, examples of which include methoxy, ethoxy, n-propoxy, iso-propoxy, n-butoxy, iso-butoxy, sec-butoxy, and t-butoxy.

The term "heteroaryl" is taken to mean a stable unsaturated five- or six-membered ring containing from 1 to 2 heteroatoms selected from the group consisting of nitrogen, oxygen and sulfur. Examples of heteroaryl include pyridinyl, pyrimidinyl, pyrazinyl, pyrrolyl, oxazolyl, isoxazolyl, imidazolyl, thiazolyl, pyridazinyl, furyl, thienyl, and the like. Preferred heteroaryl groups are thienyl, pyridinyl, and furyl.

The term "heterocycle" is taken to mean a stable saturated five- or six-membered ring containing from 1 to 3 heteroatoms selected from the group consisting of nitrogen, oxygen and sulfur. Examples of heterocycle include pyrrolidinyl, piperidinyl, piperazinyl, tetrahydrofuryl, morpholino, and the like The compounds of the present invention form pharmaceutically acceptable acid addition salts with a wide variety of organic and inorganic acids and include the physiologically acceptable salts which are often used in pharmaceutical chemistry. Such salts are also part of this invention. A "pharmaceutically-acceptable addition salt" is formed from a pharmaceutically-acceptable acid as is well known in the art. Such salts include the pharmaceutically acceptable salts listed in *Journal of Pharmaceutical Science*, 66, 2-19 (1977) which are known to the skilled artisan. Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartrate, and the like.

The present invention includes the stereoisomers and tautomers of the compounds of Formula I. Herein, the Cahn-Prelog-Ingold designations of (R)— and (S)— and the cis and trans designation of relative stereochemistry are used to refer to specific isomers and relative stereochemistry.

As with any group of pharmaceutically active compounds, some groups are preferred in their end use application. The following paragraphs define preferred classes.

a) When $R^4$ is not hydrogen, compounds which have trans stereochemistry at the 1- and 2-position are preferred.

b) When $R^4$ is not hydrogen, compounds which have the trans stereochemistry at the 1- and 2-position shown below are more preferred.

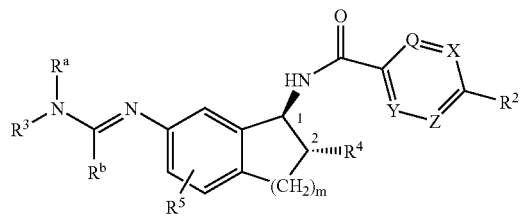

c) $R^a$ is methyl.
d) $R^5$ is hydrogen.
e) $R^4$ is hydroxy.
f) m is one.
g) $R^a$ is methyl, $R^5$ is hydrogen, $R^4$ is hydroxy, and m is one.
h) Q, X, Y, and Z are each $CR^1$ provided that at least two of Q, X, Y, and Z are CH.
i) $R^1$ is hydrogen.
j) $R^1$ is halogen.
k) $R^1$ is fluoro.
l) Q, X, Y, and Z are each CH.
m) One of Q, X, Y, and Z is CF and the others are CH.
n) Q is CF and X, Y, and Z are each CH.
p) $R^2$ is phenyl optionally substituted with from one to three substituents independently selected from the group consisting of halogen, $C_1$-$C_4$ alkoxy, $C_1$-$C_4$ alkyl, trifluoromethyl, and cyano.
q) $R^2$ is phenyl.
r) X is a straight-chain $C_1$-$C_4$ alkandiyl.
s) Y is O.
t) Y is S.
u) Z is $C_1$-$C_4$ alkyl.
v) Z is phenyl optionally substituted with one to three substituents independently selected from the group consisting of halogen, $C_1$-$C_4$ alkoxy, $C_1$-$C_4$ alkyl, trifluoromethyl, cyano, and nitro.

The preceding paragraphs may be combined to define additional preferred classes of compounds.

The compounds of Formula I in which $R^4$ is hydroxy are prepared by procedures described in Scheme A. In Scheme A all substituents, unless otherwise indicated, are as previously defined, and all reagents are well known and appreciated in the art.

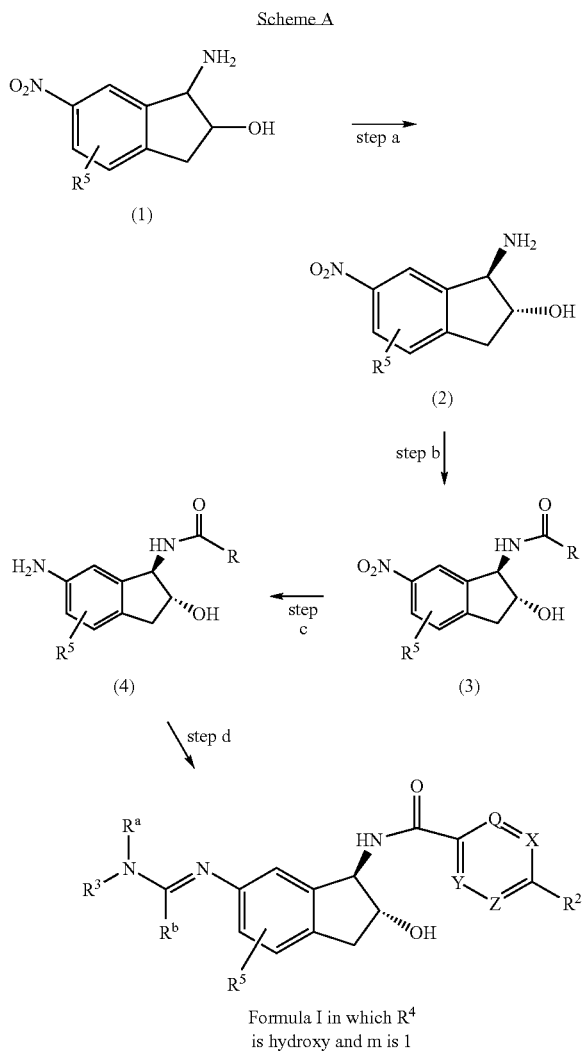

Formula I in which $R^4$ is hydroxy and m is 1

In Scheme A, step a, the compound of Formula (1) is resolved to give a substantially pure compound of Formula (2). The compound of Formula (1) is readily prepared by methods well known and appreciated in the art, such as those found in PCT Publication Nos. WO 97/25983, published 24 Jul. 1997; and WO 99/04778, published 4 Feb. 1999. As used herein the term "substantially pure" refers to enantiomeric purity. The desired stereochemistry in final compounds of Formula I may be conveniently introduced in Scheme A, step a, by resolution of compounds of Formula (1). Further processing of resolved compounds of Formula (1), via steps b, c, d, and optional step e, described infra, will result in substantially pure compounds of Formula I. Substantially pure compounds of Formula I can be prepared which are greater than 80%, preferably greater than 90%, more preferably greater than 95%, most preferably greater than 97% enantiomerically pure. The compound of Formula (1) can be resolved by chiral chromatography or by fractional crystallization of diasteriomeric acid addition salts. It is expected that a wide variety of such salts are suitable for this purpose. In practice, isomers of mandelic acid have been found to be particularly useful.

For example, the compound of Formula (1) is contacted with the selected acid. Generally, from about 0.4 molar equivalents to a large excess of the selected acid can be used with about 0.4 to 1.5 molar equivalents being preferred and with about 0.5 to 1.1 molar equivalents being more preferred. The resolution is typically carried out by crystallizing the acid addition salt from a solution. In particular, solvents such as lower alcohols, including methanol are useful. It may be advantageous to use small amounts of water with the selected solvent(s) in order to carry out the resolution in a reasonable volume. The use of an anti-solvent may also be advantageous. As used herein, the term "anti-solvent" refers to a solvent in which the salt is significantly less soluble compared to the other selected solvent(s). Preferably, when an anti-solvent is used it is miscible with the other selected solvent(s). Suitable anti-solvents include ethers, such as diethyl ether, methyl t-butyl ether, and the like, and lower alkyl acetates, such as methyl acetate, ethyl acetate, isopropyl acetate, propyl acetate, iso-butyl acetate, sec-butyl acetate, butyl acetate, amyl acetate, iso-amyl acetate, and the like, and alkanes, such as pentane, hexane, heptane, cyclohexane, and the like. When the racemic mixture is used, care should be taken in using an anti-solvent to avoid crystallization of the salt of the undesired diastereomeric salt.

Typically, the crystallization is carried out at initial temperatures of about 40° C. to reflux temperature of the selected solvent(s). The mixture is then cooled to give the salt. Seeding may be advantageous. Preferably the crystallization solution is cooled slowly. The crystallization is most conveniently cooled to temperatures of ambient temperature to about −20° C. The salt can be collected using techniques that are well known in the art, including filtration, decanting, centrifuging, evaporation, drying, and the like. The compound of Formula (2) can be used directly as the acid addition salt of the selected acid. Alternately, before use the compound of Formula (2) can be isolated as another acid addition salt after acid exchange or can by isolated as the base by extraction under basic conditions as is well known and appreciated in the art.

As is readily apparent to one skilled in the art the depicted compound of Formula (2) is of the trans configuration at the 1- and 2-positions of the indane nucleus. Cis compounds are readily prepared from such trans compounds by protection of the amine, inversion of the hydroxy center, followed by deprotection as needed. There are numerous methods which allow for inversions of hydroxy centers, such as by Mitsunobu reaction with suitable carboxylic acids, including acetic acid and benzoic acid, followed by hydrolysis. Alternately, an appropriately resolved amino-indanol may be selectively nitrated to produce a compound of Formula (2). For example, the resolved amino-indanol may be introduced to a nitrating agent, such as nitric acid or sodium nitrate. This reaction may be conducted in the presence of a strong acid, such as trifluoroacetic acid or sulfuric acid. Subsequently, the reaction may be neutralized with an appropriate base such as sodium hydroxide. Methods of nitration are well known in the art; see, for example, Organic Chemistry, Morrison & Boyd, 5th Ed (Allyn & Bacon, Inc.).

Reaction Scheme A, step b, depicts the formation of a compound of Formula (3). It is understood that the compound of Formula (3) can be one in which R is a group as desired in the final product of Formula I as defined above. R may also combine with the carbonyl to form a protecting group, such as t-BOC, which can be later removed before incorporation of an R group as desired in the final product of Formula I. The selection and use of suitable protecting groups is well known and appreciated in the art (Protecting Groups in Organic Synthesis, Theodora Greene (Wiley-Interscience)).

For example, where R is a group as desired in the final product, the coupling reaction depicted in step b is carried out using the appropriate acid or the acid halide derived therefrom. Appropriate acids include various substituted benzoic acids and acid halides, heteroaryl acids and acid halides, and various biaryl carboxylic acids and acid halides. Examples include biphenyl carboxylic acid and 3-fluorobiphenyl-4-carboxylic acid.

For example, the compound of Formula (2) is contacted with an appropriate acid to give a compound of Formula (3). Such coupling reactions are common in peptide synthesis and synthetic methods used therein can be employed. For example, well known coupling reagents, such as resin-bound reagents and carbodiimides with or without the use of well-known additives such as N-hydroxysuccinimide, 1-hydroxybenzotriazole, etc. can be used to facilitate this acylation. The reaction is conventionally conducted in an inert aprotic polar diluent such as dimethylformamide (DMF), methylene chloride (dichloromethane), chloroform, acetonitrile, tetrahydrofuran (THF), and the like. Typically the reaction is carried out at temperatures of from about 0° C. to about 60° C. and typically require from about 1 to about 24 hours. Upon reaction completion, the product of Formula (3) is recovered by conventional methods including extraction, precipitation, chromatography, filtration, trituration, crystallization and the like.

Alternatively, for example, the compound of Formula (2) is contacted with an acid halide of an appropriate acid to give a compound of Formula (3). Such acid halides are commercially available or readily prepared from the corresponding acids by methods well known in the art, such as by the action of phosphorous trichloride, phosphorous tribromide, phosphorous oxychloride, phosphorous pentachloride, thionyl chloride, thionyl bromide, or oxalyl chloride, with or without a small amount of dimethylformamide, in an inert solvent such as, toluene, methylene chloride, or chloroform; at temperatures of from about 0-80° C. The reaction is typically carried out for a period of time ranging from 1 hour to 24 hours. The acid halide can be isolated and purified or can often be used directly, that is, with or without isolation and/or purification. The coupling reactions generally use a suitable base to scavenge the acid generated during the reaction. Suitable bases include, by way of example, sodium hydroxide, potassium hydroxide, pyridine, triethylamine, N,N-diisopropylethylamine, N-methylmorpholine, and the like. The reaction is conventionally conducted in a solvent such as methylene chloride, chloroform, tetrahydrofuran and the like, or under Schotten-Baumann conditions in a solvent mixture such as methylene chloride, ethyl acetate, toluene and water. Typically the coupling reaction is carried out at temperatures of from about −20° C. to about 80° C. and typically require from about 1 to about 24 hours. Upon reaction completion, the product of Formula (3) is recovered by conventional methods including extraction, precipitation, chromatography, filtration, trituration, crystallization and the like.

Reaction Scheme A, step c, depicts the reduction of a nitro group to give a compound of Formula (4). Such reductions can be carried out by a variety of methods that are well known in the art.

For example, a compound of Formula (3) may be hydrogenated over a catalyst, such as palladium-on-carbon, to give a compound of Formula (4). Such hydrogenations are generally carried out in a solvent and a variety of solvents are suitable, for example methanol, ethanol, isopropanol, tetrahydrofuran, or ethyl acetate or mixtures thereof. The hydrogenation may be performed at an initial hydrogen pressure of 20-180 psi (137-1241 kPa). The reaction is typically carried out at temperature of about 0° C. to about 60° C. The reaction typically requires 1 hour to 3 days. The product can be isolated and purified by techniques well known in the art, such as filtration, extraction, evaporation, trituration, precipitation, chromatography, and recrystallization.

In Scheme A, step d, a compound of Formula (4) is contacted with an appropriate amidine-forming agent to give a compound of Formula I. Appropriate amidine-forming agents include 1-methylthio-1-methyl-N-(4-fluorobenzyl)-N-methylimmonium triflate and 1-methylthio-1-methyl-N-(4-fluorobenzyl)-N-methylimmonium iodide. One of ordinary skill in the art will recognize that appropriate amidine-forming agents may be prepared in advance or in situ if desired.

For example, a compound of Formula (4) is contacted with from about 1-3 equivalents of an appropriate amidine-forming agent. The reaction is generally carried out in a dry solvent such as methylene chloride, toluene, or tetrahydrofuran at temperatures of from about −20° C. to 50° C. The reaction is carried out using an appropriate base such as pyridine, collidine, or triethylamine. The reaction typically requires 1 to 18 hours. The product can be isolated and purified by techniques well known in the art, such as quenching, filtration, extraction, evaporation, trituration, precipitation, chromatography, and recrystallization.

As will be readily appreciated, where R is a protecting group introduced in step b, the protecting group can be removed after step d and the resulting amine coupled with an appropriate acid or acid halide as also described above in step b to give a compound of Formula I.

Some compounds of Formula I are intermediates for other final compounds of Formula I. For example, when $R^2$ is iodo, another reagent, for example, 2-(tributylstannyl)thiophene or 2-(tributylstannyl)pyridine, may be used to displace iodo as a leaving group and substitute a different $R^2$ group as desired in the final product.

In Scheme A, optional step e, not shown, an acid addition salt of a compound of Formula I is formed using a pharmaceutically-acceptable acid. The formation of acid addition salts is well known and appreciated in the art.

The compounds of Formula I in which $R^4$ is hydrogen are prepared from compounds of Formula (3) or from amine protected compounds of Formula (2) by deoxygenation. Such deoxygenation reactions are readily carried out using procedures well known in the art, described, for example, by Larock, Comprehensive Organic Transformations, pg. 44-52 (1999). Alternately, the compounds of Formula I in which $R^4$ is hydrogen are prepared by procedures described in Scheme B. In Scheme B all substituents, unless otherwise indicated, are as previously defined, and all reagents are well known and appreciated in the art.

Scheme B

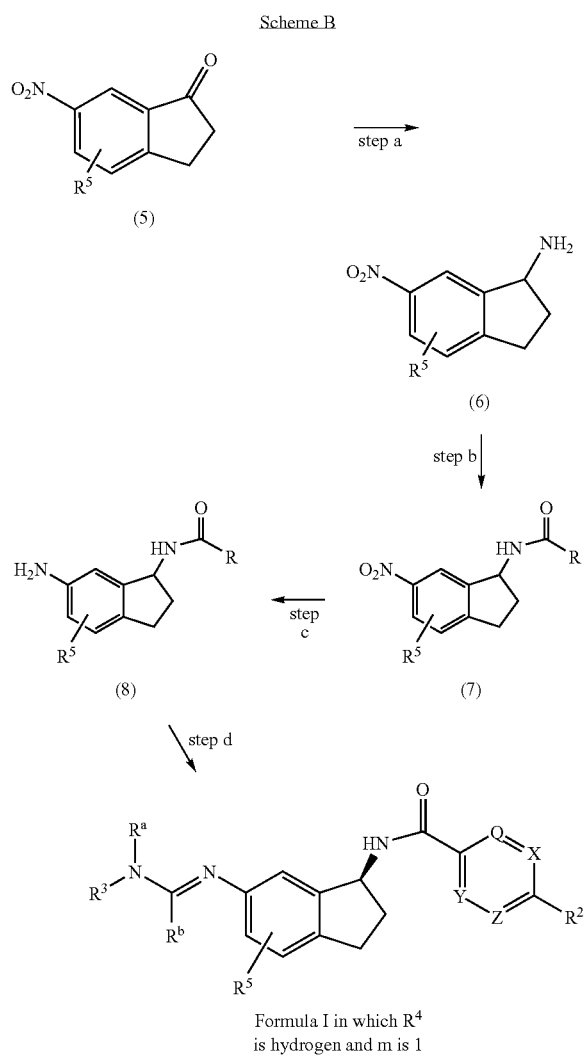

Formula I in which R⁴
is hydrogen and m is 1

Reaction Scheme B, step a, depicts the reductive amination of a compound of Formula (5) to give a compound of Formula (6). Such reductive aminations are carried out under a variety of conditions. The reaction depicted in Scheme B, step a, can be carried out using ammonia or a protected amine, such as benzyl amine, dibenzyl amine, and the like followed by deprotection to give the compound of Formula (6).

For example, a compound of Formula (5) is reacted with an excess of ammonia and sodium cyanoborohydride to give a compound of Formula (6). As is well known in the art, it may be advantageous to monitor and adjust the pH during such reactions. The reaction is carried out in a solvent, such as methanol, ethanol, isopropanol, and water or mixtures thereof. Typically the reaction is carried out at temperatures of from about 0° C. to about 60° C. and typically require from about 1 to about 24 hours. Upon reaction completion, the product of Formula (6) is recovered by conventional methods including extraction, precipitation, chromatography, filtration, trituration, crystallization, and the like.

Reaction Scheme B, steps b, c, d, and optional step e, are carried out by the methods described in Scheme A, steps b, c, d, and optional step e, to give a compound of Formula I.

The compounds of Formula I in which $R^4$ is fluoro are prepared from compounds of Formula (3) or from amine protected compounds of Formula (2) by halogenation procedures well known in the art, described, for example, by Larock, Comprehensive Organic Transformations, pg. 689-701 (1999).

The present invention is further illustrated by the following examples and preparations. These examples and preparations are illustrative only and are not intended to limit the invention in any way.

The terms used in the examples and preparations have their normal meanings unless otherwise designated. For example, "° C." refers to degrees Celsius; "M" refers to molar or molarity; "mmol" refers to millimole or millimoles; "g" refers to gram or grams; "mL" refers to milliliter or milliliters; "mp" refers to melting point; "brine" refers to a saturated aqueous sodium chloride solution; etc. In the $^1$H NMR, all chemical shifts are given in δ, unless otherwise indicated.

Coupling Procedures

Method A

2'-Chlorobiphenyl-4-carboxylic acid

Combine methyl-4-bromobenzoate (1.0 g, 4.65 mmol), 2-chlorophenylboronic acid (799 mg, 5.1 mmol), Pd(OAc)$_2$ (51 mg, 0.46 mmol) and sodium carbonate (1.5 g, 13.9 mmol) in DMF (20 mL) and water (2.0 mL) with stirring. Purge the reaction mixture with argon, add triphenylphosphine (61 mg, 0.23 mmol) and purge again with argon. Place the sealed reaction in an oil bath maintained at 80° C. and allow to stir for 1 hour. Cool the reaction to room temperature, dilute with ethyl acetate and filter through a short plug of celite with additional ethyl acetate. Wash the organics with water, dry over MgSO$_4$, filter and evaporate. Purification by flash column chromatography yields 2'-chlorobiphenyl-4-carboxylic acid methyl ester as a yellow solid. Dissolve the purified ester in THF (0.25M) and add an equal volume of 1M NaOH. Stir vigorously at room temperature for 15 hours. Upon completion, acidify the reaction with conc. HCl and extract with ethyl acetate. Evaporation of the solvent yields 762 mg (67%) of the title compound. MS (ES): m/z 231.1 (M−H).

The following compounds are prepared essentially as described above.

| | |
|---|---|
| 6-(2-Chlorophenyl)pyridine-3-carboxylic acid | MS (ES): m/z 233.9(M + H) |
| 6-(2,4-Difluorophenyl)pyridine-3-carboxylic acid | MS (ES): m/z 235.9(M + H) |
| 6-Phenylpyridine-3-carboxylic acid methyl ester | MS (ES): m/z 214.1(M + H) |
| 6-(2-Methylphenyl)pyridine-3-carboxylic acid | MS (ES): m/z 214.0(M + H) |
| 2'-Trifluoromethylbiphenyl-4-carboxylic acid | MS (ES): m/z 265.2(M − H) |
| 2-Methylbiphenyl-4-carboxylic acid | MS (ES): m/z 211.3(M − H) |
| 3-Fluorobiphenyl-4-carboxylic acid | MS (ES): m/z 215.1(M − H) |
| 2',6'-Dichlorobiphenyl-4-carboxylic acid | MS (ES): m/z 264.9(M − H) |
| 2',6'-Difluorobiphenyl-4-carboxylic acid | MS (ES): m/z 233.1(M − H) |
| 2'-Methoxybiphenyl-4-carboxylic acid | MS (ES): m/z 227.0(M − H) |
| 3,4'-Difluorobiphenyl-4-carboxylic acid | MS (ES): m/z 233.1(M − H) |
| 3,2'-Difluorobiphenyl-4-carboxylic acid | MS (ES): m/z 233.1(M − H) |
| 3-Chlorobiphenyl-4-carboxylic acid | MS (ES): m/z 231.1(M − H) |
| 4-(Thien-2-yl)phenyl-1-carboxylic acid | MS (ES): m/z 203.1(M − H) |
| 4'-Fluorobiphenyl-4-carboxylic acid (Hydrolysis in dioxane at 60° C.) | MS (ES): m/z 214.9(M − H) |

-continued

| | |
|---|---|
| 3'-Fluorobiphenyl-4-carboxylic acid (Hydrolysis in dioxane) | MS (ES): m/z 215.0(M − H) |
| 3'-Cyanobiphenyl-4-carboxylic acid (Hydrolysis with LiOH in dioxane) | MS (ES): m/z 222.0(M − H) |

Method B

5-Phenylpyrazine-2-carboxylic acid

Combine 5-chloropyrazine-2-carboxylic acid methyl ester (626 mg, 3.64 mmol), phenylboronic acid (666 mg, 5.45 mmol), cesium fluoride (55 mg, 0.36 mmol) and $Na_2CO_3$ (964 mg, 9.09 mmol) in DMF (5 mL) and water (5 mL) with stirring. Place the hetereogeneous reaction mixture, open to the air, in an oil bath maintained at 80° C. After 5 minutes of heating, add $Pd(OAc)_2$ (81 mg 0.36 mmol) in one portion and stir until reaction turns black. Cool the reaction to room temperature, dilute with ethyl acetate, and filter through a short plug of celite with additional ethyl acetate. Wash the organics with water, dry over $MgSO_4$, filter and evaporate. Purification by flash column chromatography yields 2-phenylpyrimidine-5-carboxylic acid methyl ester as a yellow solid. Dissolve the purified ester in THF (0.25M) and add an equal volume of 1M NaOH. Stir vigorously at room temperature for 15 hours. Upon completion, acidify the reaction with conc. HCl and extract with ethyl acetate. Evaporation of the solvent yields 63 mg (8%) of the title compound. $^1$H NMR (DMSO): 9.37 (s, 1H), 9.21 (s, 1H), 8.23-8.21 (m, 2H), 7.57-7.77 (m, 3H).

The following compounds are prepared essentially as described above.

| | |
|---|---|
| 2'-Fluoro-6'-trifluoromethylbiphenyl-4-carboxylic acid | MS (ES): m/z 283.1(M − H) |
| 3,2',4'-Trifluorobiphenyl-4-carboxylic acid | MS (ES): m/z 251.1(M − H) |
| 4'-Fluoro-2'-methoxybiphenyl-4-carboxylic acid | MS (ES): m/z 245.1(M − H) |
| 3-Chloro-2',4'-difluorobiphenyl-4-carboxylic acid | MS (ES): m/z 267.1(M − H) |
| 4'-Fluoro-2'-methylbiphenyl-4-carboxylic acid | MS (ES): m/z 229.0(M − H) |
| 4'-Trifluoromethylbiphenyl-4-carboxylic acid | MS (ES): m/z 265.1(M − H) |
| 2-Fluoro-4-(thien-2-yl)phenyl-1-carboxylic acid | MS (ES): m/z 221.1(M − H) |

Method C

3',4'-Difluorobiphenyl-4-carboxylic acid

Combine 3,4-difluorobenzeneboronic acid (1.0 g, 5.2 mmol), methyl-4-bromobenzoate (0.241 g, 1.73 mmol), $Pd(OAc)_2$ (0.019 g, 0.086 mmol), tetrabutylammonium bromide (0.111 g, 0.345 mmol), and potassium phosphate (0.733 g, 3.454 mmol). Purge the reaction vessel with argon and add anhydrous DMF (20 mL) to the reaction mixture. Heat the sealed reaction vessel to 120° C. with stirring until completion. Cool the reaction to room temperature, dilute with ethyl acetate, and filter through a short plug of celite with additional ethyl acetate. Wash organics with water, dry over $MgSO_4$, filter, and evaporate. Purification by flash column chromatography yields 3',4'-difluorobiphenyl-4-carboxylic acid methyl ester as a yellow solid. Dissolve the purified ester in dioxane (45 mL) and add an equal volume of 1 M aqueous NaOH. Heat the reaction vessel to 60° C. with stirring until completion. Remove the solvent by evaporation. Dissolve the residue in dichloromethane and wash with 1N aqueous hydrochloric acid. Dry the organics over $MgSO_4$, filter and evaporate to yield 0.048 g (12%) of the title compound. MS (ES): m/z 235 (M+H).

The following compounds are prepared essentially as described above.

| | |
|---|---|
| 6-(2-Fluorophenyl)pyridine-3-carboxylic acid | MS (ES): m/z 218.0(M + H) |
| 3',5'-Dimethylbiphenyl-4-carboxylic acid | MS (ES): m/z 225.0(M − H) |
| 3',5'-Difluorobiphenyl-4-carboxylic acid | MS (ES): m/z 233.0(M − H) |
| 3',5'-Dichlorobiphenyl-4-carboxylic acid | MS (ES): m/z 267.1(M$^+$) |
| 3'-Chlorobiphenyl-4-carboxylic acid | MS (ES): m/z 230.9(M − H) |
| 2',3'-Difluorobiphenyl-4-carboxylic acid | MS (ES): m/z 264.9(M − H) |
| 4'-Chlorobiphenyl-4-carboxylic acid | MS (ES): m/z 230.9(M − H) |

Method D

2',4',6'-Trimethylbiphenyl-4-carboxylic acid

Combine 1-iodo-2,4,6-trimethylbenzene (2.966 g, 12.05 mmol), 4-carboxyphenylboronic acid (1.0 g, 6.026 mmol), $Pd(OAc)_2$ (0.0067 g, 0.005 mmol), tetrabutylammonium bromide (0.388 g, 1.206 mmol), and potassium phosphate (2.557 g, 12.05 mmol). Purge the reaction vessel with argon and add anhydrous DMF (20 mL) to the reaction mixture. Heat the sealed reaction vessel to 120° C. with stirring until completion as determined by TLC. Cool reaction mixture to room temperature. Add methyl iodide (1.0 mL, 36.63 mmol) to reaction mixture with continued stirring until completion. Dilute the reaction with ethyl acetate and filter though a short plug of celite with additional ethyl acetate. Wash the organics with water, dry over $MgSO_4$, filter and evaporate. Purification by flash column chromatography yields 2',4',6'-trimethylbiphenyl-4-carboxylic acid methyl ester as a yellow solid. Dissolve the purified ester in dioxane (45 mL) and water (5 mL) containing 5 eq of LiOH with stirring at 60° C. Upon completion, evaporate the solvent, acidify the reaction mixture with hydrochloric acid, and extract with ethyl acetate. Dry the organics over $MgSO_4$, filter, and evaporate to yield 0.023 g (16%) of the title compound. MS (ES): m/z 239.1 (M−H).

The following compounds are prepared essentially as described above.

| | |
|---|---|
| 2',4',6'-Trifluorobiphenyl-4-carboxylic acid | MS (ES): m/z 251.0(M − H) |
| 2'-Fluoro-4'-trifluoromethylbiphenyl-4-carboxylic acid | MS (ES): m/z 283.0(M − H) |

Method E

2',4'-Difluorobiphenyl-4-carboxylic acid

Combine 4-carbomethoxyphenylboronic acid (1.021 g, 5.67 mmol), 1-bromo-2,4-difluorobenzene (1.000 g, 5.181 mmol.), $Pd(OAc)_2$ (0.113 g, 0.50 mmol), triphenylphosphine (0.149 g, 0.505 mmol), and sodium carbonate (1.664 g, 0.568 mmol). Purge the reaction vessel with argon. Add DMF (20 mL) and water (2.0 mL) with stirring. Place sealed reaction in an 80° C. oil bath and allow to stir for 24 hours.

Cool reaction to room temperature, dilute with ethyl acetate, and filter through a short plug of celite with additional ethyl acetate. Wash organics with water, dry over MgSO$_4$, filter, and evaporate. Purification by flash column chromatography yields 2',4'-difluorobiphenyl-4-carboxylic acid methyl ester as a yellow solid. Dissolve the purified ester in dioxane (5 mL) and add 5M NaOH (1 mL). Stir vigorously at 50° C. for 15 hours. Upon completion, acidify the reaction with conc. HCl and extract with ethyl acetate. Evaporation of the solvent yields 300 mg (24.7%) of the title compound. MS (ES): m/z 233.0 (M–H).

Method F 6-(2,6-Difluorophenyl)pyridine-3-carboxylic acid

Dissolve 6-chloropyridine-3-carboxylic acid methyl ester (6.86 g, 40 mmol) in toluene (100 mL) and heat to 90° C. Add phosphorous oxybromide (25 g, 87 mmol) in several portions and continue heating for 3 hours. Cool the reaction to room temperature and pour onto ice water. Extract the reaction with ethyl acetate and wash organics again with water then NaHCO$_3$. Combine organics, dry over MgSO$_4$, filter, and evaporate to orange solid (8.1 g, 94%) which is an 8:1 mixture of 6-bromopyridine-3-carboxylic acid methyl ester:6-chloromopyridine-3-carboxylic acid methyl ester by $^1$H NMR.

Combine the mixture as obtained above (0.225 g, 1.04 mmol) with hexamethylditin (0.375 g, 1.15 mmol), Pd(OAc)$_2$ (21 mg, 0.09 mmol), and triphenylphosphine (25 mg, 0.09 mmol) in toluene (5 mL). Purge with N$_2$ and stir at 80° C. for 18 hours. Cool reaction to room temperature. Add a solution of 1-bromo-2,6-difluorobenzene (250 mg, 1.29 mmol) in toluene (1 mL) followed by Pd(OAc)$_2$ (21 mg, 0.09 mmol) and triphenylphosphine (25 mg, 0.09 mmol). Purge with N$_2$ and stir at 80° C. for an additional 18 hours. Cool reaction to room temperature. Evaporate the solvent and purify by column chromatography (silica, 10% ethyl acetate in hexane) to give 50 mg (20% yield) of 6-(2,6-difluorophenyl)pyridine-3-carboxylic acid ethyl ester. Hydrolyze the ester with 1N sodium hydroxide solution (0.22 mL, 0.22 mmol) in methanol (3 mL) at room temperature for 3 days. Remove the volatiles under vacuum and combine the residue with 1N hydrochloric acid solution. Collect the white solid by filtration, wash with water, and dry under vacuum to give 30 mg (63% yield) of the title compound. MS (ES): m/z 235.9 (M+H).

Method G

3-Fluorobiphenyl-4-carboxylic acid

Combine methyl 2-fluoro-4-bromobenzoate (1.25 g, 5.36 mmol), phenylboronic acid (1.30 g, 10.72 mmol) and CsF (2.02 g, 13.40 mmol) in DMF (25 mL) and water (3.0 mL) with stirring. Place the hetereogeneous reaction mixture open to the air in an oil bath maintained at 80° C. After 5 minutes of heating, add Pd(OAc)$_2$ (120 mg, 0.536 mmol) in one portion and stir until reaction turns black. Cool reaction to room temperature, dilute with ethyl acetate and filter through a short plug of celite with additional ethyl acetate. Wash organics with water, dry over MgSO$_4$, filter and evaporate. Purification by flash column chromatography yields 3-fluorobiphenyl-4-carboxylic acid methyl ester as a solid. Dissolve the purified ester in THF (0.25M) and add an equal volume of 1M NaOH. Stir vigorously at room temperature for 15 hours. Upon completion, acidify the reaction with conc. HCl and extract with ethyl acetate. Evaporation of the solvent yields 965 mg (84%) of the title compound. MS (ES): m/z 214.9 (M–H).

The following compounds are prepared essentially as described above.

| | |
|---|---|
| 3-Fluoro-2'-methylbiphenyl-4-carboxylic acid | MS (ES): m/z 229.0(M – H) |
| 2'-Chloro-3-fluorobiphenyl-4-carboxylic acid | MS (ES): m/z 205.1(M – H) |
| 3-Fluoro-2'-trifluoromethylbiphenyl-4-carboxylic acid | MS (ES): m/z 283.1(M – H) |

Method H

2-Fluoro-6-phenylpyridine-3-carboxylic acid

Dissolve 2,6-difluoropyridine (5.0 mL, 5.51 mmol) in anhydrous THF (30 mL) and cool to –40° C. Add a solution of phenyl lithium (1.8 M hexanes, 30.6 mL) dropwise over 5 minutes. Stir the resulting purple reaction at –40° C. for 30 minutes and bring to room temperature. Quench the reaction with water and extract the solution with ethyl acetate several times. Combine the organic extracts, dry over MgSO$_4$, filter and evaporate onto silica gel. Purification by flash column chromatography yields 2-fluoro-6-phenylpyridine 1.0 g (12%) as a yellow oil.

Cool a solution of LDA (3.46 mmol) in anhydrous THF (6 mL) to –78° C. Cannulate the 2-fluoro-6-phenylpyridine in anhydrous THF (6 mL) to the cooled LDA solution. Stir at –78° C. for 30 minutes then bubble carbon dioxide gas through the solution for 10 minutes. Allow the reaction to come to room temperature and purge with argon. Extract the reaction with 1 M NaOH and discard the organics. Acidify the aqueous layer with conc. HCl and extract with ethyl acetate. Dry the organic layer over MgSO$_4$, filter and evaporate to yield the title compound as a light yellow solid (405 mg, 65%). MS (ES): m/z 216.1 (M–H).

Method I 3,5-Difluorobiphenyl-4-carboxylic acid

Combine 1-bromo-3,5-difluorobenzene (0.863 mL, 7.50 mmol) and phenylboronic acid (1.22 g, 10.00 mmol) and subject to conditions described in Method G to yield 1.3 g of 3,5-difluorobiphenyl.

Dissolve crude 3,5-difluorobiphenyl (1.3 g, 6.83 mmol) in THF (14 mL) and cool to –78° C. Prepare LiTMP from the addition of BuLi (1.6 M soln in hexanes, 5.33 mL) to tetramethyl piperidine (1.4 mL, 1.25 equiv) at –78° C. in THF (14 mL). Cannulate the cooled LiTMP into the cooled 3,5-difluorobiphenyl and stir the reaction at –78° C. for 1 hour. Bubble carbon dioxide gas through the solution for 5 minutes, warm the reaction to room temperature, pour into 50 mL of 1M NaOH, and extract with 50 mL EtOAc. Discard the organic layer. Acidify the remaining aqueous layer with conc. HCl and extract twice with EtOAc. Dry the organics over MgSO$_4$, filter, and evaporate to give 1.22 g of the title compound as a white solid (77%). MS (ES): m/z 233.1 (M–H).

Method J

3,2',6'-Trifluorobiphenyl-4-carboxylic acid

Combine methyl 4-bromo-2-fluorobenzoate (3.66 g, 15.75 mmol), 4,4,5,5,4',4',5',5'-octamethyl-2,2'-bi-1,3,2-dioxaborolanyl (5.0 g, 19.68 mmol) and potassium acetate (4.63 g, 47.19 mmol) in DMSO (40 mL) and purge the solution with argon. Add $PdCl_2(1,1'$-bis(diphenylphosphino) ferrocene$)_2$ (10 mol %, 1.35 g) and purge the solution with argon again. Heat the reaction to 80° C. for 3 hours and cool to room temperature. Wash the reaction with water and extract with ethyl acetate and concentrate. Redissolve the resulting black oil in 1:2 ethyl acetate:hexanes, filter through a short plug of silica gel, and concentrate to get 2-Fluoro-4-(4,4,5,5-tetramethyl-1,3,2-dioxaborolan-2-yl)benzoic acid methyl ester as a yellow oil.

Dissolve the resulting yellow oil in acetone (100 mL) and combine with $NaIO_4$ (10.1 g, 47.25 mmol), $NH_4OAc$ (3.63 g, 47.25 mmol), and water (50 mL) at room temperature. Stir at room temperature for 18 hours, transfer to a separatory funnel and extract with ethyl acetate several times. Dry the combined organics over $MgSO_4$, filter and concentrate to yield 3.0 g of 3-fluoro-4-carbomethoxybenzene boronic acid as an off-white solid.

The boronic acid obtained above (800 mg, 4.04 mmol) and 2,6-difluorobromobenzene (1.17 g, 6.06 mmol) are coupled according to the procedure described in Method G to give 380 mg of the title compound. MS (ES): m/z 251.1 (M−H).

Method K

6-Phenylpyridazine-3-carboxylic acid

Dissolve 6-Phenylpyridazin-3-ol (5.0 g, 29.06 mmol) in toluene (100 mL) and heat to 90° C. Add phosphorous oxybromide (25 g, 87.19 mmol) in several portions and heat the reaction for 30 minutes. Cool the resulting yellow solution to room temperature, pour onto ice water, and extract with ethyl acetate. Further wash the organic layers with water and 1 M NaOH, dry over $MgSO_4$, filter, and evaporate to a yellow solid. Recrystallization from $CHCl_3$ gives 2.17 g of 3-bromo-6-phenylpyridazine.

Combine 3-Bromo-6-phenylpyridazine (1.0 g, 4.25 mmol) with DMF (5 mL), MeOH (5 mL), triethylamine (1.18 mL, 8.50 mmol), and $Pd(OAc)_2$ (76 mg, 0.33 mmol) and evacuate the mixture. Add 1,1'-bis(diphenylphosphino) ferrocene (235 mg, 0.42 mmol) and again evacuate the reaction. Bubble carbon dioxide gas through the solution for 5 minutes, and place the reaction under 50 psi (345 kPa) of carbon dioxide. Heat the resulting solution at 50° C. for 18 hours. Cool the reaction to room temperature, diluted with water, and extract with ethyl acetate. Dry the organics over $MgSO_4$, filter, and evaporate onto silica gel and subject to flash column chromatography.

Hydrolysis using conditions outlined in Method A gives 80 mg of the title compound. $^1$H NMR ($CDCl_3$): 8.24 (d, 1H, J=8.8 Hz), 8.18-8.15 (m, 2H), 8.0 (d, 1H, J=9.2 Hz), 7.56-7.55 (m, 3H).

Method L

6-(4-Fluorophenyl)pyridine-3-carboxylic acid

Combine 6-bromopyridine-3-carboxylic acid methyl ester (1.03 g, 4.78 mmol), 4-fluorophenylboronic acid (1.88 g, 13.41 mmol), and cesium fluoride (2.55 g, 16.78 mmol) in DMF (25 mL) and water (4 mL) with stirring. Place the heterogeneous reaction mixture, open to the air, in an oil bath maintained at 80° C. After 5 minutes of heating, add $Pd(OAc)_2$ (150 mg, 0.67 mmol) in one portion. After 17 hours, cool the reaction to room temperature, dilute with ethyl acetate and filter through a short plug of celite with additional ethyl acetate. Wash the organics with water, dry over $MgSO_4$, filter and evaporate. Purification by flash column chromatography yields 6-(4-fluorophenyl)pyridine-3-carboxylic acid methyl ester as a yellow solid. Dissolve the purified ester in THF (0.25 M) and add an equal volume of 1 M NaOH. Stir vigorously at room temperature for 15 hours. Upon completion, acidify the reaction with conc. HCl and collect the white precipitate by filtration. Drying under vacuum yields 385 mg (37%) of the title compound. MS (ES): m/z 218.1 (M+H).

The following compound is prepared essentially as described above.

| | |
|---|---|
| 6-(Thien-2-yl)pyridine-3-carboxylic acid | MS (ES): m/z 205.9(M + H) |

Method M

6-(4-Fluoro-2-methylphenyl)pyridine-3-carboxylic acid

Combine 6-bromopyridine-3-carboxylic acid methyl ester (387 mg, 1.79 mmol), 4-fluoro-2-methylphenylboronic acid (338 mg, 2.19 mmol), $Pd(OAc)_2$ (40 mg, 0.18 mmol), cesium fluoride (27 mg, 0.18 mmol) and sodium carbonate (570 mg, 5.38 mmol) in DMF (6 mL) and water (6 mL) with stirring. Purge the reaction mixture with $N_2$, add triphenylphosphine (47 mg, 0.18 mmol), and purge again with $N_2$. Place the sealed reaction in an oil bath maintained at 80° C. and allow to stir for 17 hours. Cool the reaction to room temperature and pass through a short plug of silica gel. Wash the column with dichloromethane (100 mL) followed by aqueous methanol (100 mL, 3 methanol/1 water). Reduce the combined fractions in vacuo and suspend the residual solid in water (10 mL). Filter to remove a black solid and acidify with 1N hydrochloric acid solution to pH 4. A white precipitate forms which is collected by filtration and dried to give 306 mg (74%) of the title compound. MS (ES): m/z 231.9 (M+H).

The following compounds are prepared essentially as described above.

| | |
|---|---|
| 6-(2,4-Difluorophenyl)pyridine-3-carboxylic acid | MS (ES): m/z 236.0(M + H) |
| 6-(2-Fluorophenyl)pyridine-3-carboxylic acid | MS (ES): m/z 218.0(M + H) |
| 2'-Fluorobiphenyl-4-carboxylic acid | MS (ES): m/z 215.1(M − H) |
| 2'-Methylbiphenyl-4-carboxylic acid | MS (ES): m/z 211.2(M − H) |

Preparation 1-1

Biphenyl-4-carboxylic acid (R)-(6-(1-((4-fluorobenzyl)methylamino)ethylideneamino)-2(R)-hydroxyindan-1-yl)amide

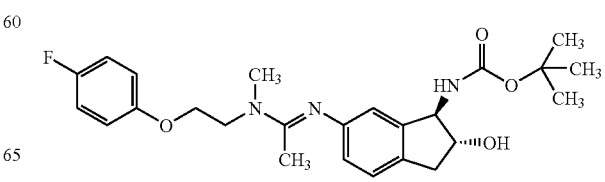

Mix 4-fluorophenol (1.0 g, 8.9 mmol), t-butyl-N-(2(R)-hydroxyethyl)carbamate (1.4 mL, 8.9 mmol) and triphenylphosphine (2.33 g, 8.9 mmol) in tetrahydrofuran (25 mL) and cool in an ice bath. Add a solution of diethylazodicarboxylate (1.4 mL, 8.9 mmol) in tetrahydrofuran (5 mL) dropwise and stir at room temperature for 18 hours. Remove the solvent under vacuum. Dissolve the residue in ether and wash with 3 portions of 1N sodium hydroxide solution. Reduce in vacuo and slurry the oil/solid in hexane and ethyl acetate. Remove the solid by filtration and reduce the filtrate in vacuo. Purify the resulting oil by chromatography using 50% ethyl acetate in hexane to give 0.94 g of (2-(4-fluorophenoxy)ethyl)carbamic acid tert-butyl ester as an oil. MS (ES): m/z 255.1 (M+H).

Dissolve (2-(4-fluorophenoxy)ethyl)carbamic acid tert-butyl ester (435 mg, 2.28 mmol) in trifluoroacetic acid (5 mL) cooled in an ice bath and stirred for 30 minutes. Reduce the solution in vacuo and dissolve in pyridine (10 mL) along with acetic anhydride (1.1 mL, 11.0 mmol). After 18 hours remove the solvent under vacuum. Dissolve the residue in dichloromethane and first extract with saturated sodium bicarbonate solution followed by a 1N HCl solution extraction. Dry and reduce the organic layer to give 272 mg of a solid that is N-(2-(4-fluorophenoxy)ethyl)acetamide which is carried without purification to the next step. Mix the N-(2-(4-fluorophenoxy)ethyl)acetamide (240 mg, 1.22 mmol) with Lawesson's reagent (296 mg, 0.73 mmol) in toluene and heat at 80° C. for 90 minutes. Remove the solvent in vacuo to give an oil. Dissolve the oil in ether and remove the solid precipitate by filtration. Add excess iodomethane (3 mL) and leave at room temperature for 17 hours. Reduce in vacuo to give an oil. Dissolve the oil in dichloromethane and wash with saturated sodium bicarbonate solution. Dry and reduce the solution to give 92 mg (0.405 mmol) of N-(2-(4-fluorophenoxy)ethyl)thioacetimidic acid methyl ester as an oil. Dissolve this product in dichloromethane and add trifluoromethanesulfonic acid methyl ester (90.5 μL, 0.8 mmol). After 18 hours remove the solvent to give an oil (129 mg). Dissolve this oil in pyridine and add (R)-(6-amino-2(R)-hydroxyindan-1-yl)carbamic acid tert-butyl ester (87 mg, 0.33 mmol). After 24 hours remove the solvent in vacuo to give an oil. Dissolve the oil in dichloromethane and wash with saturated sodium bicarbonate solution. Dry the organic layer and reduce under vacuum to give 88.9 mg of the titled compound and use as is.

Preparations 1-2 through 1-4 are prepared essentially as in Preparation 1-1 and use as is.

| Prep. # | Compound Name |
|---|---|
| 1-2 | Carbamic acid tert-butyl ester (R)-(6-(1-((2-(3,4-difluorophenoxy)ethyl)methylamino)ethylideneamino)-2(R)-hydroxyindan-1-yl)amide |
| 1-3 | Carbamic acid tert-butyl ester (R)-(6-(1-((2-(4-fluoro-3-methylphenoxy)ethyl)methylamino)ethylideneamino)-2(R)-hydroxyindan-1-yl)amide |
| 1-4 | Carbamic acid tert-butyl ester (R)-(6-(1-((2-(2-fluorophenoxy)ethyl)methylamino)ethylideneamino)-2(R)-hydroxyindan-1-yl)amide |

Preparation 2-1

Carbamic acid tert-butyl ester (R)-(6-(1-(morpholin-4-yl)ethylideneamino)-2(R)-hydroxyindan-1-yl)amide

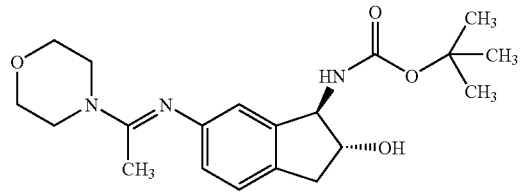

Dissolve morpholine (1 g, 11.5 mmol) in pyridine (10 mL) along with acetic anhydride (10 mL, 100.0 mmol). After 4 hours remove the solvent under vacuum. Dissolve the residue in dichloromethane and first extract with saturated sodium bicarbonate solution followed by a 1N HCl solution extraction. Dry and reduce the organic layer to give 355 mg of an oil that is 1-morpholin-4-yl-ethanone which is carried without purification to the next step. Mix the 1-morpholin-4-yl-ethanone (347 mg, 2.7 mmol) with Lawesson's reagent (652 mg, 1.6 mmol) in toluene and heat at 80° C. for 4 hours. Remove the solvent in vacuo to give an oil. Dissolve the oil in ether and remove the solid precipitate by filtration. Add excess iodomethane (3 mL) and leave at room temperature for 17 hours. Collect the precipitate by filtration yielding 365 mg of solid. Combine this solid with (R)-(6-amino-2(R)-hydroxyindan-1-yl)carbamic acid tert-butyl ester (317 mg, 1.2 mmol) in pyridine (10 mL). After 24 hours remove the solvent in vacuo to give an oil. Dissolve the oil in dichloromethane and wash with saturated sodium bicarbonate solution. Dry the organic layer and reduce under vacuum to give a residue that is purified by chromatography eluting with 2% methanol in chloroform to give 224 mg of the titled compound. $^1$H-NMR (CDCl$_3$) δ 7.05 (1H, d), 6.55 (2H, m), 5.04 (1H, d), 4.85 (1H, t), 4.40 (1H, q), 4.28 (1H, s), 3.75 (4H, m), 3.45 (4H, m), 3.22 (1H, dd), 2.95 (1H, dd), 1.84 (3H, s), 1.45 (9H, s).

Preparation 3-1

Carbamic acid tert-butyl ester (R)-(6-(1-((2-methoxyethyl)methylamino)ethylideneamino)-2(R)-hydroxyindan-1-yl)amide

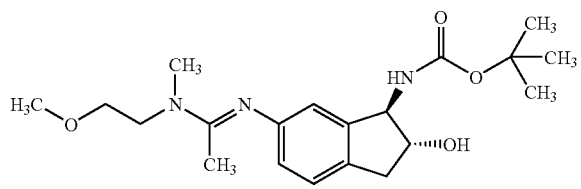

Dissolve N-(2-methoxyethyl)methylamine (5.81 g, 65.18 mmol) in 40 mL of pyridine at 0° C. and add acetic anhydride dropwise. After 30 minutes raise the reaction to room temperature and stir for 24 hours. Remove the solvent in vacuo and dissolve the residue in methylene chloride and wash with 5N HCl. Dry the organic layer with magnesium sulfate. Filter and remove the solvent in vacuo to give 4.23 g of crude N-(2-methoxyethyl)-N-methylacetamide. Dissolve this crude material (4.23 g, 32.25 mmol) in 50 mL of toluene and add Lawesson's reagent (6.5197 g, 16.12 mmol) to the mixture. Heat the reaction to 75° C. and allow it to stir for 18 hours. Remove the solvent in vacuo. Triturate the residue with a 1:1 mixture of diethyl ether/pentane three times decanting carefully from the residual solids. Combine the decanted layers and remove the solvent in vacuo to afford 2.13 g of crude N-(2-methoxyethyl)-N-methylthioacetamide. Dissolve this crude material (2.13 g, 14.47 mmol) in 50 mL diethyl ether and add methyl trifluoromethanesulfonate (2.49 g, 15.19 mmol) and allow the reaction to stir for 21 hours. Decant the diethyl ether from the oil and triturate the oil with diethyl ether (3×). Remove any excess diethylether from the oily residue in vacuo to obtain 2.92 g of crude triflic acid salt of (2-methoxyethyl)methyl(1-methylsulfanylethyl)amine as a black oil. Dissolve this black oil (2.92 g, 9.38 mmol) in 50 mL of pyridine and add (R)-(6-amino-2(R)-hydroxyindan-1-yl)carbamic acid tert-butyl ester (2.46 g, 9.31 mmol) and allow the reaction to stir at room temperature for 23 hours. Remove the solvent in vacuo and dissolve the residue in methylene chloride and wash with saturated aqueous sodium hydrogencarbonate. Dry the organic layer with magnesium sulfate. Filter and remove the solvent in vacuo. Purify the residue by Biotage chromatography (10% MeOH/EtOAc to 25% MeOH/EtOAc) to afford 1.304 g of the titled product (37% yield). MS (ES): m/z 378.2 (M+H).

Preparation 3-2 is prepared essentially as Preparation 3-1.

| Prep. # | Compound Name | MS (ES): m/z |
|---|---|---|
| 3-2 | Carbamic acid tert-butyl ester (R)-(6-(1-((2-propoxyethyl)methylamino)ethylideneamino)-2(R)-hydroxyindan-1-yl)amide | 406.3(M + H) |

EXAMPLE 1-1

Biphenyl-4-carboxylic acid (R)-(6-(1-((2-methoxyethyl)methylamino)ethylideneamino)-2(R)-hydroxyindan-1-yl)amide

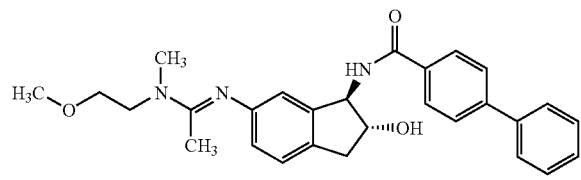

Dissolve carbamic acid tert-butyl ester (R)-(6-(1-((2-methoxyethyl)methylamino)ethylideneamino)-2(R)-hydroxyindan-1-yl)amide (153.6 mg, 0.407 mmol) in excess TFA at 0° C. and allow to stir for 1 hour. Remove the solvent in vacuo. Dissolve the residue in 10 mL methylene chloride and add triethylamine (411.8 mg, 4.07 mmol) and biphenyl-4-carboxylic acid 2,5-dioxopyrrolidin-1-yl ester (118.3 mg, 0.400 mmol). Allow the reaction mixture to stir for 21 hours. Dilute the reaction mixture with methylene chloride and wash it with saturated aqueous sodium hydrogen carbonate (1×) and brine (1×). Dry the organic layer with magnesium sulfate. Filter and remove the solvent in vacuo to give 162.1 mg of crude product. Purify via Biotage chromatography (30% MeOH/EtOAc) to afford 93.1 mg of the titled product as an oil (50% yield). MS (ES): m/z 458.3(M+H).

Examples 1-2 through 1-14 are prepared essentially as Example 1-1.

| Ex. # | Compound Name | MS (ES): m/z |
|---|---|---|
| 1-2 | Biphenyl-4-carboxylic acid (R)-(6-(1-((2-propoxyethyl)methylamino)ethylideneamino)-2(R)-hydroxyindan-1-yl)amide | 486.3 (M + H) |
| 1-3 | 2'-Fluorobiphenyl-4-carboxylic acid (R)-(6-(1-((2-methoxyethyl)methylamino)ethylideneamino)-2(R)-hydroxyindan-1-yl)amide | 475.1 (M + H) |
| 1-4 | 3-Fluorobiphenyl-4-carboxylic acid (R)-(6-(1-((2-methoxyethyl)methylamino)ethylideneamino)-2(R)-hydroxyindan-1-yl)amide | 476.4 (M + H) |
| 1-5 | 3,2'-Difluorobiphenyl-4-carboxylic acid (R)-(6-(1-((2-methoxyethyl)methylamino)ethylideneamino)-2(R)-hydroxyindan-1-yl)amide | 494.2 (M + H) |
| 1-6 | 3,2',6'-Trifluorobiphenyl-4-carboxylic acid (R)-(6-(1-((2-methoxyethyl)methylamino)ethylideneamino)-2(R)-hydroxyindan-1-yl)amide | 512.2 (M + H) |
| 1-7 | 3,2'-Difluorobiphenyl-4-carboxylic acid (R)-(6-(1-(morpholin-4-yl)ethylideneamino)-2(R)-hydroxyindan-1-yl]amide | 492.3 (M + H) |
| 1-8 | Biphenyl-4-carboxylic acid (R)-(6-(1-((2-(4-fluorophenoxy)ethyl)methylamino)ethylideneamino)-2(R)-hydroxyindan-1-yl)amide | 538.4 (M + H) |
| 1-9 | 4'-Fluorobiphenyl-4-carboxylic acid (R)-(6-(1-((2-(4-fluorophenoxy)ethyl)methylamino)ethylideneamino)-2(R)-hydroxyindan-1-yl)amide | 556.4 (M + H) |
| 1-10 | 2',6'-Difluorobiphenyl-4-carboxylic acid (R)-(6-(1-((2-(4-fluorophenoxy)ethyl)methylamino)ethylideneamino)-2(R)-hydroxyindan-1-yl)amide | 574.4 (M + H) |
| 1-11 | Biphenyl-4-carboxylic acid (R)-(6-(1-((2-(3,4-difluorophenoxy)ethyl]methylamino)ethylideneamino)-2(R)-hydroxyindan-1-yl)amide | 556.4 (M + H) |
| 1-12 | 3-Fluorobiphenyl-4-carboxylic acid (R)-(6-(1-((2-(3,4-difluorophenoxy)ethyl)methylamino)ethylideneamino)-2(R)-hydroxyindan-1-yl)amide | 574.2 (M + H) |
| 1-13 | Biphenyl-4-carboxylic acid (R)-(6-(1-((2-(4-fluoro-3-methylphenoxy)ethyl)methylamino)ethylideneamino)-2(R)-hydroxyindan-1-yl)amide | 552.5 (M + H) |
| 1-14 | Biphenyl-4-carboxylic acid (R)-(6-(1-((2-(2-fluorophenoxy)ethyl)methylamino)ethylideneamino)-2(R)-hydroxyindan-1-yl)amide | 538.3 (M + H) |

EXAMPLE 2-1

4-Bromophenyl-1-carboxylic acid (R)-(6-(1-((2-methoxyethyl)methylamino)ethylideneamino)-2(R)-hydroxyindan-1-yl)amide

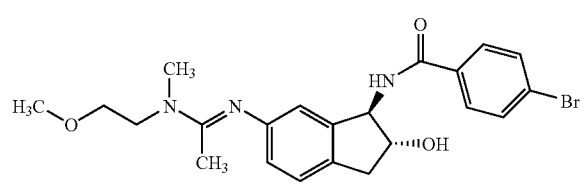

To a mixture of thioacetamide (10.04 g, 133.6 mmol) and potassium carbonate (45.80 g, 331.4 mmol) in 100 mL tetrahydrofuran at 0° C. add phthaloyl chloride (28.49 g, 140.3 mmol) dropwise. Raise the reaction temperature to 25° C. after 2 hours and allow it to stir for an additional 2 hours before cooling the reaction mixture to 0° C. again. Quench the reaction by adding 125 mL of ice water dropwise. Extract the reaction mixture with EtOAc (2×). Dry the organic layer with magnesium sulfate and remove the solvent in vacuo to yield 3.7 g of 2-thioacetylisoindole-1,3-dione as a crude reddish solid. See also *J. Org. Chem.* 1997, 62, 3808-3809. $^1$H NMR (CDCl3) δ 8.00 (2 H, m), 7.82 (2 H, m), 3.10 (3 H, s).

Dissolve N-(2-methoxymethyl)methylamine (101.0 mg, 1.13 mmol) in 20 mL diethyl ether at 25° C. To this add 2-thioacetyl-isoindole-1,3-dione (243.0 mg, 1.18 mmol) and allow to stir for 22 hours. Filter the reaction mixture and add methyl trifluoromethanesulfonate (194.7 mg, 1.19 mmol) to the filtrate and allow to stir for an additional 18 hours. Decant the diethyl ether from the oil and triturate the oil with diethyl ether (3×). Remove any excess diethyl ether from the oily residue in vacuo to obtain 320.4 mg of crude triflic acid salt of (2-methoxyethyl)methyl(1-methylsulfanylethyl) amine as an oil. Dissolve this crude product (161.1 mg, 0.483 mmol) in 5 mL pyridine and add N-(R)-(6-amino-2(R)hydroxyindan-1-yl)-4-bromobenzamide (115.1 mg, 0.331 mmol). Allow the reaction to stir at 25° C. for 22 hours. Remove the solvent in vacuo and partition the residue between methylene chloride and saturated aqueous sodium hydrogencarbonate. Dry the organic layer with magnesium sulfate. Filter and remove the solvent in vacuo to give 40.8 mg of crude product. Purify via silica gel chromatography (5% MeOH/CHCl$_3$ to 30% MeOH/CHCl$_3$) to afford 40.8 mg of the titled product (27% yield). MS (ES): m/z 460.2(M+ H).

Examples 2-2 and 2-3 are prepared essentially as Example 2-1.

| Ex. # | Compound Name | MS (ES): m/z |
|---|---|---|
| 2-2 | 4-Bromophenyl-1-carboxylic acid (R)-(6-(1-((2-methoxyethyl)amino)ethylideneamino)-2(R)-hydroxyindan-1-yl)amide | 446.1 (M + H) |
| 2-3 | 4-Bromophenyl-1-carboxylic acid (R)-(6-(1-((2-methoxypropyl)amino)ethylideneamino)-2(R)-hydroxyindan-1-yl)amide | 460.2 (M + H) |

EXAMPLE 3-1

4-Bromophenyl-1-carboxylic acid (R)-(6-(1-((2-methoxypropyl)methylamino)ethylideneamino)-2(R)-hydroxyindan-1-yl)amide

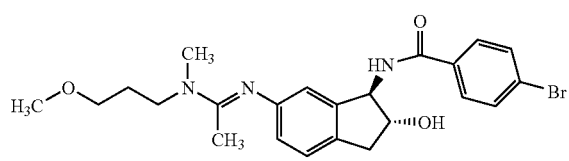

Dissolve 3-methoxypropylamine (154.1 mg, 1.73 mmol) in 20 mL diethyl ether at 25° C. To this add 2-thioacetyl-isoindole-1,3-dione (370.7 mg, 1.81 mmol) and allow to stir for 18 hours. Filter the reaction mixture and add methyl trifluoromethanesulfonate (298.1 mg, 1.82 mmol) to the filtrate and allow to stir for an additional 24 hours. Decant the diethyl ether from the oil and triturate the oil with diethyl ether (3×). Remove any excess diethyl ether from the oily residue in vacuo to obtain 320.4 mg of crude triflic acid salt of N-(3-methoxypropyl)thioacetimidic acid methyl ester as an oil. Dissolve this crude product (379.8 mg, 1.22 mmol) in methylene chloride and wash it with saturated aqueous sodium hydrogen carbonate. Dry the organic layer with magnesium sulfate. Add methyl trifluoromethanesulfonate (210.2 mg, 1.28 mmol) to the filtrate and allow to stir for an additional 24 hours. Remove the solvent in vacuo and triturate the oil with diethyl ether (3×). Remove any excess diethyl ether from the oily residue in vacuo to obtain 296.5 mg of crude triflic acid salt of (3-methoxypropyl)methyl(1-methylsulfanylethyl)amine as an oil. Dissolve this crude material (99.5 mg, 0.30 mmol) in 5 mL pyridine and add N-(R)-(6-amino-2(R)-hydroxyindan-1-yl)-4-bromobenzamide (105.7 mg, 0.304 mmol). Allow the reaction to stir at 25° C. for 18 hours. Remove the solvent in vacuo and partition the residue between methylene chloride and saturated aqueous sodium hydrogen carbonate. Dry the organic layer with magnesium sulfate. Filter and remove the solvent in vacuo to give 40.8 mg of crude product. Purify via silica gel chromatography (5% MeOH/CHCl$_3$ to 30% MeOH/CHCl$_3$) to afford 50.0 mg of the titled product (35% yield). MS (ES): m/z 474.1 (M+H).

Examples 3-2 through 3-7 are prepared essentially as Example 3-1.

| Ex. # | Compound Name | MS (ES): m/z |
|---|---|---|
| 3-2 | 4-Bromophenyl-1-carboxylic acid (R)-(6-(1-((2-phenoxyethyl)methylamino)ethylideneamino)-2(R)-hydroxyindan-1-yl)amide | 522.2 (M + H) |
| 3-3 | 4-Bromophenyl-1-carboxylic acid (R)-(6-(1-((2-ethoxyethyl)methylamino)ethylideneamino)-2(R)-hydroxyindan-1-yl)amide | 474.1 (M + H) |
| 3-4 | 4-Bromophenyl-1-carboxylic acid (R)-(6-(1-((2-propoxyethyl)methylamino)ethylideneamino)-2(R)-hydroxyindan-1-yl)amide | 488.1 (M + H) |
| 3-5 | 4-Bromophenyl-1-carboxylic acid (R)-(6-(1-((2-methoxy-1-methylethyl)methylamino)ethylideneamino)-2(R)-hydroxyindan-1-yl)amide | 474.1 (M + H) |
| 3-6 | 4-Bromophenyl-1-carboxylic acid (R)-(6-(1-((2-benzyloxyethyl)methylamino)ethylideneamino)-2(R)-hydroxyindan-1-yl)amide | 536.2 (M + H) |
| 3-7 | 4-Bromophenyl-1-carboxylic acid (R)-(6-(1-((2-isopropoxyethyl)methylamino)ethylideneamino)-2(R)-hydroxyindan-1-yl)amide | 488.2 (M + H) |

EXAMPLE 4-1

4-Bromophenyl-1-carboxylic acid (R)-(6-(1-(((R)-2-methoxy-2-phenylethyl)methylamino)ethylideneamino)-2(R)-hydroxyindan-1-yl)amide

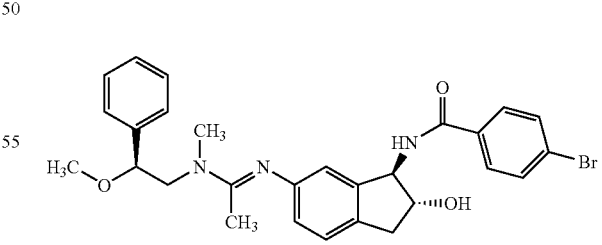

Dissolve (R)-(−)-2-methoxy-2-phenylethanol (1.1177 g, 7.34 mmol) and triethylamine (1.11 g, 11.02 mmol) in 20 mL methylene chloride at 0° C. Dissolve para-toluenesolfonyl chloride (1.4498 g, 7.60 mmol) in 10 mL methylene chloride and add it dropwise to the reaction. After 30 minutes raise the reaction to room temperature and allow it to stir for 24 hours. Dilute the reaction with methylene chloride and wash it with water (1×), 1N HCl (1×), saturated aqueous sodium hydrogen carbonate (1×) and brine (1×). Dry the organic layer with magnesium sulfate. Filter and remove the solvent in vacuo to give 2.01 g of crude toluene-4-sulfonic acid 2-methoxy-2-phenylethyl ester. Dissolve this crude material (2.01 g, 6.56 mmol) and di-tert-butyl iminodicarboxylate (1.495 g, 6.88 mmol) in 25 mL acetonitrile. Add potassium tert-butoxide (777.1 mg, 6.92 mmol) to the reaction mixture and heat it to reflux for 24 hours. Cool the reaction to room temperature and remove the solvent in vacuo. Dissolve the residue in methylene chloride and wash it with water (1×) and brine (1×). Dry the organic layer with magnesium sulfate. Filter and remove the solvent in vacuo to give 2.34 g of crude material. Purify via Biotage chromatography (5% EtOAc/hexanes) to afford 607.9 mg of (2-methoxy-2-phenylethyl)dicarbamic acid tert-butyl ester as an oil (26% yield). MS (ES): m/z 458.3(M+H).

Dissolve (2-methoxy-2-phenylethyl)dicarbamic acid tert-butyl ester (607.9 mg, 1.73 mmol) in excess trifluoroacetic acid at 0° C. and allow to stir for 1 hour. Remove the solvent in vacuo to afford crude 2-methoxy-2-phenylethylamine. Dissolve this crude material in 10 mL of pyridine at 0° C. and add acetic anhydride (194.2 mg, 1.90 mmol) dropwise. After 30 minutes raise the reaction to room temperature and stir for 24 hours. Remove the solvent in vacuo and dissolve the residue in methylene chloride and wash with 5N HCl. Dry the organic layer with magnesium sulfate. Filter and remove the solvent in vacuo to give 384.1 mg of crude N-(2-methoxy-2-phenylethyl)acetamide. Dissolve this crude material (384.1 mg, 1.99 mmol) in 20 mL of toluene and add Lawesson's reagent (404.47 mg, 1.01 mmol) to the mixture. Heat the reaction to 75° C. and allow it to stir for 22 hours. Remove the solvent in vacuo. Triturate the residue with a 1:1 mixture of diethyl ether/pentane three times decanting carefully from the residual solids. Combine the decanted layers and remove the solvent in vacuo to afford 125.5 mg of crude N-(2-methoxy-2-phenylethyl)thioacetamide. Dissolve this crude material (125.5 mg, 0.600 mmol) in 10 mL methylene chloride and add methyl trifluoromethanesulfonate (108.2 mg, 0.660 mmol) and allow the reaction to stir for 21 hours. Decant the diethyl ether from the oil and triturate the oil with diethyl ether (2×). Remove any excess diethyl ether from the oily residue in vacuo to obtain 102.3 mg of crude triflic acid salt of N-(2-methoxy-2-phenylethyl)thioacetimidic acid methyl ester. Dissolve this crude product (102.3 mg, 0.274 mmol) in methylene chloride and wash it with saturated aqueous sodium hydrogen carbonate. Dry the organic layer with magnesium sulfate. Add methyl trifluoromethanesulfonate (56.19 mg, 0.342 mmol) to the filtrate and allow to stir for an additional 24 hours. Remove the solvent in vacuo and triturate the oil with diethyl ether (3×). Remove any excess diethyl ether from the oily residue in vacuo to obtain 75.0 mg of crude triflic acid salt of (2-methoxy-2-phenylethyl)methyl(1-methylsulfanylethyl)amine as an oil. Dissolve this crude material (75.0 mg, 0.194 mmol) in 10 mL pyridine and add N-(R)-(6-amino-2(R)-hydroxyindan-1-yl)-4-bromobenzamide (66.0 mg, 0.190 mmol). Allow the reaction to stir at 25° C. for 18 hours. Remove the solvent in vacuo and partition the residue between methylene chloride and saturated aqueous sodium hydrogen carbonate. Dry the organic layer with magnesium sulfate. Filter and remove the solvent in vacuo to give 70.0 mg of crude product. Purify via Biotage chromatography (2% MeOH/EtOAc) to afford 38.6 mg of the titled product (38% yield). MS (ES): m/z 538.2 (M+H).

Examples 4-2 through 4-6 are prepared essentially as Examples 4-1 using the appropriate commercially available alcohol.

| Ex. # | Compound Name | MS (ES): m/z |
|---|---|---|
| 4-2 | 4-Bromophenyl-1-carboxylic acid (R)-(6-(1-((3-methoxybutyl)methylamino)ethylideneamino)-2(R)-hydroxyindan-1-yl) amide | 488.3 (M + H) |
| 4-3 | 4-Bromophenyl-1-carboxylic acid (R)-(6-(1-((2-hexyloxyethyl)methylamino)ethylideneamino)-2(R)-hydroxyindan-1-yl)amide | 531.3 (M + H) |
| 4-4 | 4-Bromophenyl-1-carboxylic acid (R)-(6-(1-((4-benzyloxybutyl)methylamino)ethylideneamino)-2(R)-hydroxyindan-1-yl)amide | 564.1 (M + H) |
| 4-5 | 4-Bromophenyl-1-carboxylic acid (R)-(6-(1-((3-methoxy-3-methylbutyl)methylamino)ethylideneamino)-2(R)-hydroxyindan-1-yl)amide | 502.1 (M + H) |
| 4-6 | 4-Bromophenyl-1-carboxylic acid (R)-(6-(1-((2-isobutoxyethyl)methylamino)ethylideneamino)-2(R)-hydroxyindan-1-yl)amide | 503.1 (M + H) |

EXAMPLE 5-1

Biphenyl-1-carboxylic acid (R)-(6-(1-((2-pentoxyethyl)methylamino)ethylideneamino)-2(R)-hydroxyindan-1-yl)amide

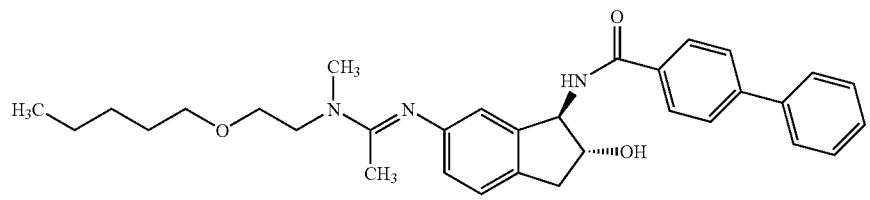

Dissolve the crude triflic acid salt of (1-methylsulfanylethyl)(2-pentoxyethyl)methylamine (192.1 mg, 0.523 mmol) and biphenyl-4-carboxylic acid (R)-(6-amino-2(R)-hydroxyindan-1-yl)amide (170.8 mg, 0.496 mmol) in 10 mL pyridine and allow it to stir for 22 hours. Remove the solvent in vacuo and partition the residue between methylene chloride and saturated aqueous sodium hydrogen carbonate. Dry the organic layer with magnesium sulfate. Filter and remove the solvent in vacuo to give 112.3 mg of crude product. Purify via Biotage chromatography (10% MeOH/EtOAc 25% MeOH/EtOAc) to afford 27.8 mg of the titled product (11% yield). MS (ES): m/z 514.5 (M+H).

Examples 5-2 and 5-3 are prepared essentially as Example 5-1.

| Ex. # | Compound Name | MS (ES): m/z |
|---|---|---|
| 5-2 | Biphenyl-1-carboxylic acid (R)-(6-(1-((2-butoxyethyl)methylamino)ethylideneamino)-2(R)-hydroxyindan-1-yl)amide | 500.5 (M + H) |
| 5-3 | Biphenyl-4-carboxylic acid (R)-(6-(1-((2-cyclohexyloxyethyl)methylamino)ethylideneamino)-2(R)-hydroxyindan-1-yl)amide | 526.3 (M + H) |

EXAMPLE 6-1

Biphenyl-4-carboxylic acid (R)-(6-(1-((2-methylsulfanylethyl)methylamino)ethylideneamino)-2(R)-hydroxyindan-1-yl)amide

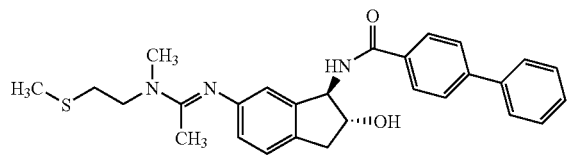

Dissolve 2-(methylthio)ethylamine (5.6601 g, 62.08 mmol) in 20 mL pyridine at 0° C. and add acetic anhydride (31.69 g, 310.38 mmol) dropwise. After 30 minutes raise the reaction to room temperature and stir for 21 hours. Remove the solvent in vacuo and dissolve the residue in methylene chloride and wash with 5N HCl. Dry the organic layer with magnesium sulfate. Filter and remove the solvent in vacuo to give 4.174 g of crude N-(2-methylsulfanylethyl)acetamide. Dissolve the crude material (2.032 g, 15.25 mmol) in 10 mL DMF and add it dropwise to a suspension of sodium hydride (404.34 mg, 16.85 mmol) in 10 mL DMF. Allow the reaction to stir for 24 hours at room temperature. Quench the reaction with MeI (2.598 g, 18.30 mmol). Partition the reaction mixture between EtOAc and brine and wash the EtOAc layer with brine (2×). Dry the organic layer with magnesium sulfate. Filter and remove the solvent in vacuo to give 948.9 mg of very crude N-methyl-N-(2-methylsulfanylethyl)acetamide. Dissolve this crude material (299.4 mg, 2.03 mmol) in 10 mL of toluene and add Lawesson's reagent (417.2 g, 1.03 mmol) to the mixture. Heat the reaction to 75° C. and allow it to stir for 27 hours. Remove the solvent in vacuo. Triturate the residue with diethyl ether three times decanting carefully from the residual solids. Combine the decanted layers and remove the solvent in vacuo to afford 491.7 mg of crude N-methyl-N-(2-methylsulfanylethyl)thioacetamide. Dissolve this crude material (491.7 mg, 3.01 mmol) in 10 mL diethyl ether and add MeI (316.95 mg, 2.23 mmol) and allow the reaction to stir for 21 hours. Decant the diethyl ether from the oil and triturate the oil with diethyl ether (3×). Remove any excess diethyl ether from the oily residue in vacuo to obtain 165.6 mg of crude HI salt of methyl-(2-methylsulfanylethyl)(1-methylsulfanylethyl)amine as a yellow solid. Dissolve this crude material (165.6 mg, 0.542 mmol) in 10 mL of pyridine and add (R)-(6-amino-2(R)-hydroxyindan-1-yl)carbamic acid tert-butyl ester (197.6 mg, 0.748 mmol) and allow the reaction to stir at room temperature for 22 hours. Remove the solvent in vacuo and dissolve the residue in methylene chloride and wash with saturated aqueous sodium hydrogen carbonate. Dry the organic layer with magnesium sulfate. Filter and remove the solvent in vacuo. Purify the residue by Biotage chromatography (5% MeOH/EtOAc to 20% MeOH/EtOAc) to afford 81.6 mg of (R)-6-(1-(methyl-(2-methylsulfanylethyl)amino)ethylideneamino)-2(R)-hydroxyindan-1-yl) carbamic acid tert-butyl ester (28%). MS (ES): m/z394.1 (M+H). Prepare the final product as in Example 1-1 to afford 82.4 mg of crude material. Purify via silica gel column chromatography (2% MeOH/CHCl₃ to 5% MeOH/CHCl₃) to afford 50.9 mg of the titled product as an oil (52% yield). MS (ES): m/z 474.2(M+H).

EXAMPLE 7-1

3,2'-Difluorobiphenyl-4-carboxylic acid (R)-(6-(1-((2-methylsulfanylethyl)methylamino)ethylideneamino)-2(R)-hydroxyindan-1-yl)amide

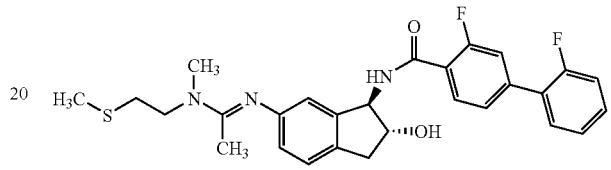

Dissolve the crude HI salt of methyl-(2-methylsulfanylethyl)(1-methylsulfanylethyl)amine (90.1 mg, 0.295 mmol) and 3,2'-difluorobiphenyl-4-carboxylic acid (R)-(6-amino-2(R)-hydroxyindan-1-yl)amide (101.3 mg, 0.266 mmol) in 10 mL pyridine. Allow the reaction to stir at 25° C. for 21 hours. Remove the solvent in vacuo and partition the residue between methylene chloride and saturated aqueous sodium hydrogen carbonate. Dry the organic layer with magnesium sulfate. Filter and remove the solvent in vacuo to give 91.5 mg of crude product. Purify via silica gel column chromatography (2% MeOH/CHCl₃ to 5% MeOH/CHCl₃) to afford 30.5 mg of the titled product (22% yield). MS (ES): m/z 510.1(M+H).

Example 7-2 is prepared essentially as Example 7-1.

| Ex. # | Compound Name | MS (ES): m/z |
|---|---|---|
| 7-2 | 3,2'-Difluorobiphenyl-4-carboxylic acid (R)-(6-(1-((2-tert-butylsulfanylethyl)methylamino)ethylideneamino)-2(R)-hydroxyindan-1-yl)amide | 552.1 (M + H) |

EXAMPLE 8-1

3,2'-Difluorobiphenyl-4-carboxylic acid (R)-(6-((1-thiomorpholin-4-yl)ethylideneamino)-2(R)-hydroxyindan-1-yl)amide

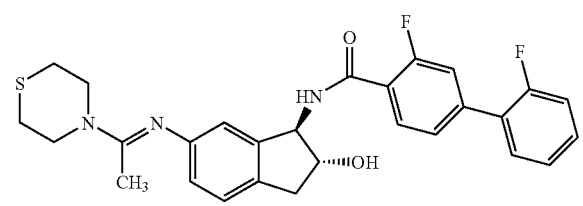

Dissolve crude 1-thiomorpholin-4-yl-ethanethione (869.4 mg, 5.39 mmol) in 20 mL diethyl ether and add MeI (501.0 mg, 3.53 mmol). Allow the reaction to stir at room temperature for 18 hours. Decant the diethyl ether from the oil and triturate the oil with diethyl ether (2×). Remove any excess diethyl ether from the oily residue in vacuo to obtain 142.2 mg of crude HI salt of 4-(1-methylsulfanylethyl)thiomorpholine as a solid. Dissolve this crude material (142.2 mg, 0.469 mmol) in 20 mL of pyridine and add (R)-(6-amino-2(R)-hydroxyindan-1-yl)carbamic acid tert-butyl ester (110.0 mg, 0.469 mmol) and allow the reaction to stir at room temperature for 22 hours. Remove the solvent in vacuo and dissolve the residue in methylene chloride and wash with saturated aqueous sodium hydrogen carbonate. Dry the organic layer with magnesium sulfate. Filter and remove the solvent in vacuo. Purify via silica gel column chromatography (2% MeOH/CHCl₃) to afford 74.1 mg of crude (R)-6-((1-thiomorpholin-4-yl)ethylideneamino)-2(R)-hydroxyindan-1-yl)carbamic acid tert-butyl ester. Crude MS (ES): m/z392.2 (M+H). Dissolve this crude material (74.1 mg, 0.189 mmol) in excess TFA at 0° C. and allow to stir for 1 hour. Remove the solvent in vacuo. Dissolve the residue in 10 mL methylene chloride and add triethylamine (191.5 mg, 1.89 mmol) and 3,2'-difluorobiphenyl-4-carboxylic acid 2,5-dioxopyrrolidin-1-yl ester (64.3 mg, 0.194 mmol). Allow the reaction mixture to stir for 17 hours. Dilute the reaction mixture with methylene chloride and wash it with saturated aqueous sodium hydrogen carbonate (1×) and brine (1×). Dry the organic layer with magnesium sulfate. Filter and remove the solvent in vacuo to give 73.6 mg of crude product. Purify via silica gel column chromatography (2% MeOH/CHCl₃) to afford 3.2 mg of the titled product. (3% yield). MS (ES): m/z 508.2 (M+H).

EXAMPLE 9-1

4-Bromophenyl-1-carboxylic acid (R)-(6-(1-((2-tert-butoxyethyl)amino)ethylideneamino)-2(R)-hydroxy-indan-1-yl)amide

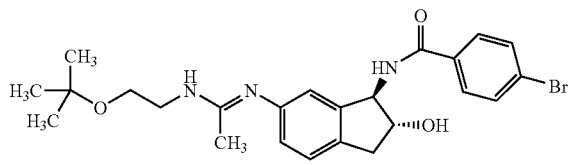

Dissolve ethylene glycol mono-tert-butyl ether (2.62 g, 22.17 mmol) and triethylamine (3.36 g, 11.02 mmol) in 40 mL methylene chloride at 0° C. Dissolve para-toluenesulfonyl chloride (4.2277 g, 22.17 mmol) in 10 mL methylene chloride and add it dropwise to the reaction. After 30 minutes raise the reaction to room temperature and allow it to stir for 17 hours. Dilute the reaction with methylene chloride and wash it with water (1×), 1N HCl (1×), saturated aqueous sodium hydrogen carbonate (1×) and brine (1×). Dry the organic layer with magnesium sulfate. Filter and remove the solvent in vacuo to give 4.6387 g of crude toluene-4-sulfonic acid 2-tert-butoxyethyl ester. Dissolve this crude material (1.2423 g, 4.56 mmol) and di-benzyl iminodicarboxylate (1.4385 g, 5.04 mmol) (see *Synthesis*, 1988, 992-994) in 20 mL acetonitrile. Add potassium tert-butoxide (575.9 mg, 5.13 mmol) to the reaction mixture and heat it to reflux for 24 hours. Cool the reaction to room temperature and remove the solvent in vacuo. Dissolve the residue in methylene chloride and wash it with water (1×) and brine (1×). Dry the organic layer with magnesium sulfate. Filter and remove the solvent in vacuo to give 1.9215 g of crude material. Purify via Biotage chromatography (EtOAc/Hexanes) to afford 387.8 mg of (2-tert-butoxyethyl)dicarbamic acid benzyl ester (22%). MS (ES): m/z 386.3 (M+H).

Dissolve (2-tert-butoxyethyl)dicarbamic acid benzyl ester (387.8 mg, 1.01 mmol) and 5% Pd/C (0.212 g) in absolute ethanol and expose it to 60 psi of H₂ for 18 hours. Filter the reaction mixture over a pad of celite. Acidify the filtrate with 5N HCl and concentrate in vacuo to obtain 139.4 mg of a crude residue containing the HCl salt of 2-tert-butoxyethylamine. Dissolve this crude material (139.4 mg, 0.852 mmol) in 10 mL pyridine at 25° C. To this add 2-thioacetylisoindole-1,3-dione (180.53 mg, 0.88 mmol) and allow to stir for 23 hours. Concentrate the reaction mixture in vacuo and dissolve the residue in methylene chloride and wash it with 1N HCl (1×). Dry the organic layer with magnesium sulfate. Filter and remove the solvent in vacuo to give 266.9 mg of crude product. Triturate this crude material in diethyl ether and remove the solids by filtration. Concentrate the filtrate in vacuo to afford 176.2 mg of a crude solid. Purify via Biotage chromatography to afford 74.1 mg of N-(2-tert-butoxyethyl)thioacetamide. Dissolve this thioacetamide (74.1 mg, 0.423 mmol) in 20 mL methylene chloride and add methyl trifluoromethanesulfonate (76.3 mg, 0.465 mmol). Allow the reaction mixture to stir for an additional 21 hours. Decant the diethyl ether from the oil and triturate the oil with diethyl ether (3×). Remove any excess diethyl ether from the oily residue in vacuo to obtain 60.3 mg of crude triflic acid salt of N-(2-tert-butoxyethyl)thioacetimidic acid methyl ester as an oil. Dissolve this crude product (60.3 mg, 0.625 mmol) in 10 mL pyridine and add N-(R)-(6-amino-2(R)-hydroxyindan-1-yl)-4-bromobenzamide (62.5 mg, 0.180 mmol). Allow the reaction to stir at 25° C. for 22 hours. Remove the solvent in vacuo and partition the residue between methylene chloride and saturated aqueous sodium hydrogen carbonate. Dry the organic layer with magnesium sulfate. Filter and remove the solvent in vacuo to give 31.4 mg of crude product. Purify via Biotage chromatography (10% MeOH/EtOAc) to afford 6.6 mg of the titled product (8% yield). MS (ES): m/z 488.1 (M+H).

EXAMPLE 10-1

Biphenyl-4-carboxylic acid (R)-(6-(1-((2-tert-butoxyethyl)methylamino)ethylideneamino)-2(R)-hydroxyindan-1-yl)amide

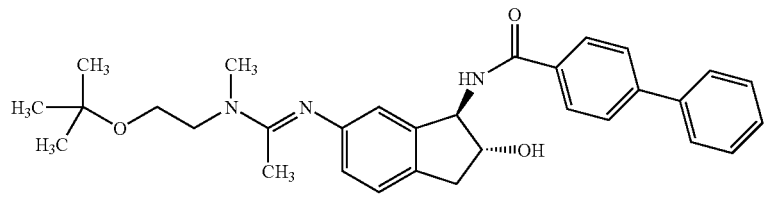

Dissolve the crude HI salt of (2-tert-butoxyethyl)methyl-(1-methylsulfanylethyl)amine (obtained using the crude HCl salt of 2-tert-butoxyethylamine, referenced in Example 9-1, using the methodology detailed in Example 6-1) (297.1 mg, 0.897 mmol) in 20 mL pyridine and add biphenyl-4-carboxylic acid (R)-(6-amino-2(R)-hydroxyindan-1-yl)amide (290.7 mg, 0.844 mmol). Allow the reaction to stir for 18 hours. Remove the solvent in vacuo and dissolve the residue in methylene chloride and wash with saturated aqueous sodium hydrogen carbonate. Dry the organic layer with magnesium sulfate. Filter and remove the solvent in vacuo to afford 248.7 mg of crude product. Purify the residue by Biotage chromatography (10% MeOH/EtOAc to 25% MeOH/EtOAc) to afford 91.7 mg of the titled product (22% yield). MS (ES): m/z 500.5 (M+H).

EXAMPLE 11-1

3,2'-Difluorobiphenyl-1-carboxylic acid (R)-(6-(1-((2-tert-butoxyethyl)amino)ethylideneamino)-2(R)-hydroxyindan-1-yl)amide

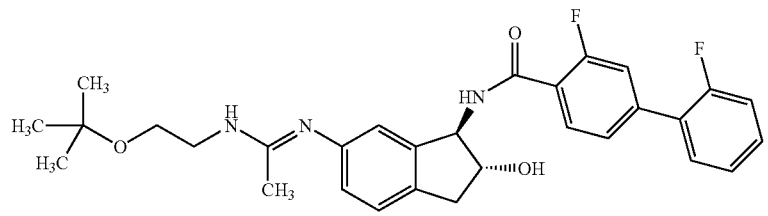

Dissolve the crude HI salt of N-(2-tert-butoxyethyl)thioacetimidic acid methyl ester (see Example 9-1) (91.2 mg, 0.287 mmol) in 10 mL pyridine and add 3,2'-difluorobiphenyl-4-carboxylic acid (R)-(6-amino-2(R)-hydroxyindan-1-yl)amide (102.4 mg, 0.269 mmol). Allow the reaction to stir for 20 hours. Remove the solvent in vacuo and dissolve the residue in methylene chloride and wash with saturated aqueous sodium hydrogen carbonate. Dry the organic layer with magnesium sulfate. Filter and remove the solvent in vacuo to afford 71.6 mg of crude product. Purify the residue by Biotage chromatography (5% MeOH/EtOAc to 20% MeOH/EtOAc) to afford 45.7 mg of the titled product (33% yield). MS (ES): m/z 522.2 (M+H).

EXAMPLE 12-1

3,2'-Difluorobiphenyl-4-carboxylic acid (R)-(6-(1-((2-(1-methylcyclopropoxy)ethyl)methylamino)ethylideneamino)-2(R)-hydroxyindan-1-yl)amide

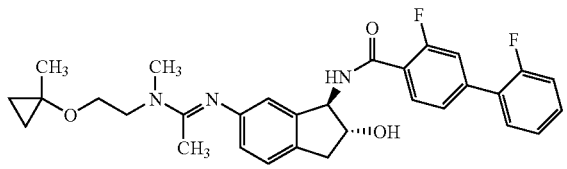

Dissolve 2-(1-methylcyclopropoxy)ethanol (362.3 mg, 3.12 mmol) (see Tet. Lett. 1999, 40, 8647-8650) and triethylamine (473.4 mg, 4.68 mmol) in 10 mL methylene chloride at 0° C. Dissolve para-toluenesulfonyl chloride (596.1 mg, 3.12 mmol) in 10 mL methylene chloride and add it dropwise to the reaction. After 30 minutes raise the reaction to room temperature and allow it to stir for 24 hours. Dilute the reaction with methylene chloride and wash it with water (1×), 1N HCl (1×), saturated aqueous sodium hydrogen carbonate (1×) and brine (1×). Dry the organic layer with magnesium sulfate. Filter and remove the solvent in vacuo to give 670.1 mg of crude toluene-4-sulfonic acid 2-(1-methylcyclopropoxy)ethyl ester. Dissolve N-methylacetamide (176.9 mg, 2.42 mmol) in 5 mL tetrahydrofuran and add it dropwise to a slurry of sodium hydride (122.9 mg, 3.07 mmol) in 5 mL tetrahydrofuran. Allow the reaction to stir at room temperature for 22 hours. Dissolve the crude toluene-4-sulfonic acid 2-(1-methylcyclopropoxy)ethyl ester (670.1 mg, 2.48 mmol) in 5 mL tetrahydrofuran and add it dropwise to the reaction mixture. After the addition is complete, heat the reaction to reflux and allow it to stir for 26 hours. Cool the reaction and remove the solvent in vacuo. Dissolve the residue in methylene chloride and wash with brine (1×). Dry the organic layer with magnesium sulfate. Filter and remove the solvent in vacuo to afford 276.9 mg of crude material. Purify the residue by Biotage chromatography (50% EtOAc/Hexanes to 30% MeOH/EtOAc) to afford 83.3 mg of N-methyl-N-(2-(1-methylcyclopropoxy)ethyl) acetamide. Dissolve this material (83.3 mg, 0.486 mmol) in 10 mL of toluene and add Lawesson's reagent (102.5 mg, 0.253 mmol) to the mixture. Heat the reaction to 75° C. and allow it to stir for 24 hours. Remove the solvent in vacuo. Triturate the residue with diethyl ether three times decanting carefully from the residual solids. Combine the decanted layers and remove the solvent in vacuo to afford 47.0 mg of crude N-methyl-N-(2-(1-methylcyclopropoxy)ethyl)thioacetamide. Dissolve this crude material (47.0 mg, 0.251 mmol) in 10 mL diethyl ether, add MeI (excess) and allow the reaction to stir for 21 hours. Decant the diethyl ether from the oil and triturate the oil with diethyl ether (2×). Remove any excess diethyl ether from the oily residue in vacuo to obtain 46.5 mg of crude HI salt of methyl-(2-(1-methylcyclopropoxy)ethyl)-(1-methylsulfanylethyl)amine as an oil. Dissolve this crude material (46.5 mg, 0.141 mmol) in 10 mL of pyridine and add 3,2'-difluorobiphenyl-4-carboxylic acid (R)-(6-amino-2(R)-hydroxyindan-1-yl)amide (49.6 mg, 0.130 mmol) and allow the reaction to stir at room temperature for 20 hours. Remove the solvent in vacuo and dissolve the residue in methylene chloride and wash with saturated aqueous sodium hydrogen carbonate. Dry the organic layer with magnesium sulfate. Filter and remove the solvent in vacuo to give 39.2 mg of crude product. Purify via silica gel column chromatography (2% MeOH/CHCl$_3$) to afford 10.7 mg of the titled product (15% yield). MS (ES): m/z 534.2 (M+H).

EXAMPLE 13-1

4-Bromophenyl-1-carboxylic acid (R)-(6-(1-((2-methoxyethyl)methylamino)propylideneamino)-2(R)-hydroxyindan-1-yl)amide

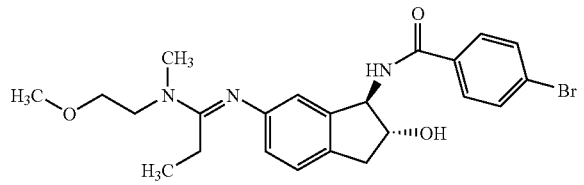

Dissolve N-(2-methoxymethyl)methylamine (996.1 mg, 11.17 mmol) and triethylamine (1.3536 g, 13.404 mmol) in 10 mL methylene chloride and add propionic anhydride (1.526 g, 11.73 mmol) to the reaction mixture. Allow the reaction to stir at room temperature for 20 hours. Dilute the reaction mixture with methylene chloride and wash it with water (1×), saturated aqueous sodium hydrogencarbonate (1×), 1N HCl (1×) and brine (1×). Dry the organic layer with magnesium sulfate. Filter and remove the solvent in vacuo to give 854.9 mg of crude N-(2-methoxyethyl)-N-methyl-propionamide. Dissolve this material (77.8 mg, 5.36 mmol) in 20 mL of toluene and add Lawesson's reagent (1.091 g, 2.70 mmol) to the mixture. Heat the reaction to 75° C. and allow it to stir for 22 hours. Remove the solvent in vacuo. Triturate the residue with diethyl ether three times decanting carefully from the residual solids. Combine the decanted layers and remove the solvent in vacuo to afford 446.6 mg of crude N-(2-methoxyethyl)-N-methylthiopropionamide. Dissolve this crude material in 20 mL methylene chloride, add methyl trifluoromethanesulfonate (477.2 mg, 2.91 mmol) and allow the reaction to stir for 26 hours. Remove the solvent in vacuo and triturate the oil with diethyl ether (3×). Remove any excess diethyl ether from the oily residue in vacuo to obtain 873.8 mg of crude triflic acid salt of (2-methoxyethyl)methyl-(1-methylsulfanylpropyl)amine as an oil. Dissolve this crude material (131.3 mg, 0.404 mmol) in 10 mL of pyridine and add 3,2'-difluorobiphenyl-4-carboxylic acid (R)-(6-amino-2(R)-hydroxyindan-1-yl)amide (111.9 mg, 0.322 mmol) and allow the reaction to stir at room temperature for 24 hours. Remove the solvent in vacuo and dissolve the residue in methylene chloride and wash with saturated aqueous sodium hydrogen carbonate. Dry the organic layer with magnesium sulfate. Filter and remove the solvent in vacuo to give the crude product. Purify via Biotage chromatography (10% MeOH/EtOAc) to afford 66.1 mg of the titled product (44% yield). MS (ES): m/z 474.2 (M+H).

EXAMPLE 14-1

Biphenyl-4-carboxylic acid (R)-(6-(1-((2-methylsulfanylethyl)amino)ethylideneamino)-2(R)-hydroxyindan-1-yl)amide

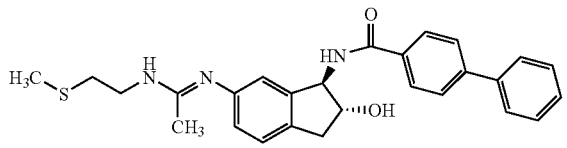

Dissolve N-(2-methylsulfanylethyl)acetamide (352.7 mg, 2.65 mmol)(see Example 6-1) in 50 mL of toluene and add Lawesson's reagent (537.0 g, 1.33 mmol) to the mixture. Heat the reaction to 75° C. and allow it to stir for 26 hours. Remove the solvent in vacuo. Triturate the residue with diethyl ether three times decanting carefully from the residual solids. Combine the decanted layers and remove the solvent in vacuo to afford 400.9 mg of crude N-(2-methylsulfanylethyl)thioacetamide. Dissolve this crude material (400.9 mg, 2.69 mmol) in 10 mL methylene chloride, add MeI (458.18 mg, 3.228 mmol) and allow the reaction to stir for 24 hours. Remove the solvent in vacuo and triturate the oil with diethyl ether (3×). Remove any excess diethyl ether from the oily residue in vacuo to obtain 526.8 mg of crude HI salt of N-(2-methylsulfanylethyl)thioacetimidic acid methyl ester as an oil. Dissolve this crude material (71.1 mg, 0.244 mmol) in 10 mL of pyridine and add biphenyl-4-carboxylic acid (R)-(6-amino-2(R)-hydroxyindan-1-yl)amide (75.3 mg, 0.2.19 mmol) and allow the reaction to stir at room temperature for 22 hours. Remove the solvent in vacuo and dissolve the residue in methylene chloride and wash with saturated aqueous sodium hydrogen carbonate. Dry the organic layer with magnesium sulfate. Filter and remove the solvent in vacuo to give 156.0 mg of crude product. Purify via Biotage chromatography (10% MeOH/EtOAc to 25% MeOH/EtOAc) to afford 62.4 mg of the titled product (62% yield). MS (ES): m/z 460.2 (M+H).

EXAMPLE 15-1

4-Bromophenyl-1-carboxylic acid (R)-(6-(1-((2-methoxy-1(R)-phenylethyl)methylamino)ethylidene-amino) 2(R)-hydroxyindan-1-yl)amide

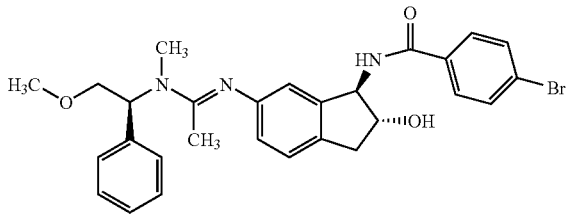

Dissolve (R)-(−)-2-phenylgylcinol (1.006 g, 7.33 mmol) and triethylamine (1.781 g, 17.60 mmol) in 10 mL methylene chloride at 0° C. Add acetyl chloride (1.209 g, 15.40 mmol) to the reaction mixture. After 30 minutes allow the reaction to warm to 25° C. and Allow to stir for 12 hours. Remove the solvent in vacuo and dissolve the residue in ethyl acetate. Wash the organic layer with water (1×), 1N HCl (1×) and brine (1×). Separate the organic layer and dry it over magnesium sulfate. Filter and remove the solvent in vacuo to give 1.053 g of the crude acetic acid 2-acetylamino-2-phenylethyl ester in 65% yield. Dissolve this product (1.053 g, 4.76 mmol) in 20 mL methanol and add an excess of potassium carbonate. Allow the reaction to stir at 25° C. for 18 hours. Remove the solvent in vacuo and triturate the residue with methanol. Filter off all solids and wash with copious amounts of methanol. Remove the solvent in vacuo to obtain 717.4 mg of the crude N-(2-hydroxy-1-phenyl-ethyl)acetamide as a yellow oil in 84% yield. Dissolve this crude product (717.4 mg, 4.00 mmol) in 10 mL tetrahydrofuran and add it dropwise to a suspension of sodium hydride (376.2 g, 9.405 mmol) in 20 mL tetrahydrofuran at 25° C. and allow it to stir for 18 hours. Add excess MeI to the reaction mixture and allow it to stir for and additional 26 hours. Remove the solvent in vacuo and dissolve the residue in methylene chloride. Wash the organic layer with water (1×) and brine (1×) and dry it over magnesium sulfate. Remove the solvent in vacuo to afford 625.2 mg of the crude N-(2-methoxy-1-phenylethyl)-N-methylacetamide as a yellow oil. Dissolve 426.1 mg of this crude product in 20 mL toluene and add Lawesson's reagent (424.0 mg, 1.05 mmol)

to the mixture. Heat the mixture to 80° C. for 21 hours. Remove the solvent in vacuo and triturate the residue with a 1:1 mixture of diethyl ether/pentane (3×). Combine the decanted organic layers and remove the solvent in vacuo to afford 230.3 mg of crude titled product. Purify via column chromatography (silica gel, 15% EtOAc/Hexanes) to afford 143.3 mg of N-(2-methoxy-1-phenylethyl)-N-methylthioacetamide as an oil in 31% yield. MS (ES): m/z 224 (M+H).

Add methyl trifluoromethanesulfonate (110.56 mg, 0.674 mmol) to a solution of N-(2-methoxy-1-phenylethyl)-N-methylthioacetamide in 10 mL diethyl ether and allow the reaction to stir at 25° C. for 18 hours. Decant the diethyl ether from the oil and triturate the oil with diethyl ether (3×). Remove any excess diethyl ether from the oily residue in vacuo to obtain 235.5 mg of crude thioimidate of N-(2-methoxy-1-phenylethyl)-N-methylthioacetamide as an oil. Dissolve this crude product (235.5 mg, 0.608 mmol) in 20 mL pyridine and add N-(R)-(6-amino-2(R)-hydroxyindan-1-yl)-4-bromobenzamide (201.7 mg, 0.581 mmol). Allow the reaction to stir at 25° C. for 23 hours. Remove the solvent in vacuo and partition the residue between methylene chloride and saturated aqueous sodium hydrogen carbonate. Dry the organic layer with magnesium sulfate. Filter and remove the solvent in vacuo to give 257.0 mg of crude product. Purify via Biotage chromatography (5% MeOH/EtOAc) to afford 162.9 mg of the titled product as a cream colored solid (52% yield). MS (ES): m/z 537(M+H).

Examples 15-2 through 15-5 are prepared essentially as Example 15-1.

| Ex. # | Compound Name | MS (ES): m/z |
|---|---|---|
| 15-2 | 4-Bromophenyl-1-carboxylic acid (R)-(6-(1-((2-methoxy-1-phenylethyl)methylamino)ethylideneamino)-2(R)-hydroxyindan-1-yl)amide | 552.1 (M + H) |
| 15-3 | 3,2'-Difluorobiphenyl-4-carboxylic acid (R)-(6-(1-(2-tertbutoxyethyl)methylamino)ethylideneamino)-2(R)-hydroxyindan-1-yl)amide | 536.2 (M + H) |
| 15-4 | 3,2'-Difluorobiphenyl-4-carboxylic acid (R)-(6-(1-((2-cyclopropoxyethyl)methylamino)ethylideneamino)-2(R)-hydroxyindan-1-yl)amide | 520.0 (M + H) |
| 15-5 | 3,2'-Difluorobiphenyl-4-carboxylic acid (R)-(6-(1-((2-(1,1-dimethylpropoxy)ethyl)methylamino)ethylideneamino)-2(R)-hydroxyindan-1-yl)amide | 550.2 (M + H) |

EXAMPLE 16-1

Biphenyl-4-carboxylic acid (R)-(6-(1-((2-(pyridin-2-ylsulfanylethyl)amino)ethylideneamino)-2(R)-hydroxyindan-1-yl)amide To a mixture of 2-aminoethanethiol hydrochloride (4.07 g, 35.6 mmol) in dioxane (75 mL) at 50° C., add sodium hydride (60% in mineral oil, 2.84 g, 71.0 mmol) at room temperature under nitrogen. Allow the reaction to stir for 5 minutes and add 2-chloropyridine (3.5 mL, 37 mmol) to the mixture. Reflux the mixture for 24 hours and cool to room temperature. Add water (100 mL), and methylene chloride (300 mL) to this mixture. Extract the aqueous layer with methylene chloride (3×50 mL). Wash the combined organic phase with brine (200 mL), dry over magnesium sulfate, filter and concentrate to an orange oil. Flash chromatography on silica gel eluting with 50% (80:18:12 CHCl$_3$/MeOH/concentrated NH$_4$OH)/methylene chloride affords the title compound as a yellow oil (1.67 g, 30%). $^1$H NMR (CDCl$_3$) δ 8.43 (m, 1H), 7.44 (m, 1H), 7.21 (m, 1H), 6.97 (m, 1H), 3.30 (m, 2H), 3.02 (m, 2H); MS (ES) m/z:=155 [C$_7$H$_{10}$N$_2$S+H]$^+$. Add 2-thioacetyl-isoindole-1,3-dione (0.7 g, 3.2 mmol) to a solution of 2-(pyridin-2-ylsulfanyl)ethylamine (0.5 g, 3.2 mmol) in CHCl$_3$ (20 mL) at 0° C. After 15 minutes, concentrate and purify the residue by flash chromatography on silica gel eluting with 40% EtOAc/Hex containing 2% NH$_4$OH to afford N-(2-(pyridin-2-ylsulfanyl)ethyl)thioacetamide (0.4 g, 58%) as a pale yellow oil. $^1$H NMR (CDCl$_3$) δ 10.26 (br s, 1H), 8.41-8.43 (m, 1H), 7.57 (dt, J=7.35 Hz, J=1.8 Hz, 1H), 7.31 (dd, J=8.10 Hz, J=0.96 Hz, 1H), 7.09-7.13 (m, 1H), 3.87-3.92 (m, 2H), 3.40-3.43 (m, 2H), 2.53 (s, 3H); MS (APCI): m/z 213 (M+H).

Add methyl trifluoromethanesulfonate (65.5 mg, 0.4 mmol) to a solution of N-(2-(pyridin-2-ylsulfanyl)ethyl)thioacetamide (85.0 mg, 0.4 mmol) in methylene chloride (10 mL) under nitrogen. Stir the reaction mixture at room temperature for 5 minutes and remove the solvent under reduced pressure to give N-[2-(pyridin-2-ylsulfanyl)ethyl)thioacetimidic acid methyl ester (0.4 mmol) as a colorless oil. MS (ES): m/z 227 (M+H).

Dissolve N-[2-(pyridin-2-ylsulfanyl)ethyl)thioacetimidic acid methyl ester (0.4 mmol) in dry pyridine (5.0 mL) and add biphenyl-4-carboxylic acid (R)-(6-amino-2(R)-hydroxy-indan-1-yl)amide (0.15 g, 0.4 mmol). The reaction mixture was stirred at room temperature for 12 hours. Remove the solvent under reduced pressure and purify the residue by flash chromatography on silica gel eluting with 20% MeOH/EtOAc to afford the title compound (140 mg, 67%) as a colorless oil. $^1$H NMR (CDCl$_3$) δ 8.40 (s, 1H), 7.89 (d, J=8.4 Hz, 2H), 7.60-7.68 (m, 4H), 7.36-7.51 (m, 4H), 7.11 (d, J=7.8 Hz, 1H), 7.00 (t, J=5.4 Hz, 1H), 6.68-6.73 (m, 4H), 5.95 (br s, 1H), 5.28 (s, 1H), 4.52 (q, J=7.5 Hz, 1H), 3.68 (br s, 2H), 3.39 (br s, 2H), 3.30 (dd, J=15.6 Hz, J=7.8 Hz, 1 H), 2.94 (dd, J=15.3 Hz, J=7.8 Hz, 1H), 1.78 (s, 3H); MS (APCI): m/z 523 (M+H)$^+$.

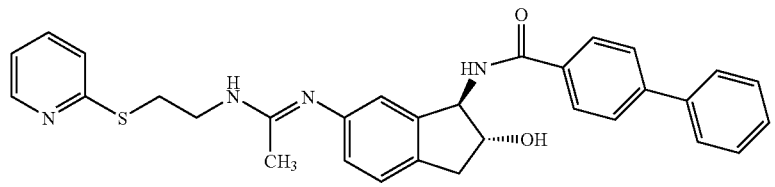

EXAMPLE 17-1

Biphenyl-4-carboxylic acid (R)-(6-(1-((2-(pyridin-2-ylsulfanylethyl)amino)ethylideneamino)-2(R)-hydroxyindan-1-yl)amide

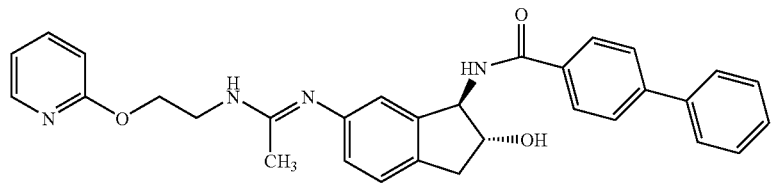

Add sodium hydride (60% in mineral oil, 6.63 g, 166 mmol) to a solution of 2-hydroxyethylamine (10.0 mL, 166 mmol) in dioxane (150 mL) at room temperature under nitrogen. After stirring for 10 minutes at room temperature, add 2-chloropyridine (15.6 mL, 166 mmol) and heat the reaction mixture to reflux. After stirring at reflux for 14 hours, cool the reaction mixture to room temperature and dilute with water (100 mL) and methylene chloride (200 mL). Extract the aqueous layer with methylene chloride (2×100 mL). Wash the combined organic phase with brine (200 mL), dry over magnesium sulfate, filter, and concentrate to an orange oil. Flash chromatography on silica gel eluting with 50% of a (80:18:2 $CHCl_3$/MeOH/concentrated $NH_4OH$) solution in methylene chloride affords 2-phenoxyethylamine as a yellow oil (17.9 g, 78%). $^1H$ NMR ($CDCl_3$) δ 8.09-8.15 (m, 1H), 7.53-7.56 (m, 1H), 6.80-6.85 (m, 1H), 6.70-6.75 (m, 1H), 4.27-4.31 (m, 2H), 3.06-3.10 (m, 2H); MS (ES): m/z 139 (M+H).

Add 2-(pyridin-2-yloxy)ethylamine (500 mg, 3.62 mmol) to a solution of 2-thioacetyl-isoindole-1,3-dione (743 mg, 3.62 mmol) in $CHCl_3$ (18 mL) at 0° C. After stirring for 15 minutes, concentrate the solution, redissolve in ethyl acetate (25 mL), filter, and concentrate again. Flash chromatography ($SiO_2$, 1:1 EtOAc/Hex) gives N-(2-(pyridin-2-yloxy)ethyl)thioacetamide (350 mg, 49%) as a beige/pink solid. $^1H$ NMR ($CDCl_3$) δ 8.79 (br s, 1H), 8.10-8.08 (m, 1H), 7.58-7.65 (m, 1H), 6.92-7.00 (m, 1H), 6.76-6.82 (m, 1H), 4.57-4.65 (m, 2H), 3.98-4.05 (m, 2H), 2.56 (s, 3H).

Add N-(2-(pyridin-2-yloxy)ethyl)thioacetamide (50 mg, 0.25 mmol) and methyl trifluoromethanesulfonate (0.028 mL, 0.25 mmol) in methylene chloride (1.5 mL), and stir at room temperature. After 10 minutes, concentrate the solution to dryness. To this residue, add a solution of biphenyl-4-carboxylic acid (R)-(6-amino-2(R)-hydroxyindan-1-yl)amide (95 mg, 0.275 mmol) in pyridine (3 mL). Stir the resulting solution at room temperature for 18 hours and remove the pyridine under vacuum. Flash chromatography ($SiO_2$, 1:1 EtOAc/Hex to 80:18:2 $CHCl_3$/MeOH/concentrated $NH_4OH$) gives the title compound (21 mg, 17%) as a white solid. $^1H$ NMR ($CDCl_3$) δ 7.88-7.95 (m, 2H), 7.65-7.74 (m, 2H), 7.60-7.70 (m, 2H), 7.40-7.53 (m, 3H), 7.24-7.26 (m, 2H), 7.02-7.99 (m, 2H), 6.626.70 (m, 1H), 5.35-5.42 (m, 1H), 4.55-4.62 (m, 1H), 3.78-3.90 (m, 4H), 3.30-3.43 (m, 1H), 2.92-3.08 (m, 1H), 2.02 (s, 3H); MS (ES): m/z 507 (M+H).

The compounds of the present invention can be administered alone or in the form of a pharmaceutical composition, that is, combined with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be Formulated and administered in the form of their pharmaceutically acceptable salts, for purposes of stability, convenience, solubility, and the like. In practice, the compounds of Formula I are usually administered in the form of pharmaceutical compositions, that is, in admixture with pharmaceutically acceptable carriers or diluents.

Thus, the present invention provides pharmaceutical compositions comprising a compound of Formula I and a pharmaceutically acceptable diluent. The present invention also provides suitable packaging, including a label, containing the pharmaceutical compositions comprising a compound of Formula I.

The compounds of Formula I can be administered by a variety of routes. In effecting treatment of a patient afflicted with disorders described herein, a compound of Formula I can be administered in any form or mode which makes the compound bioavailable in an effective amount, including oral and parenteral routes. For example, compounds of Formula I can be administered orally, by inhalation, subcutaneously, intramuscularly, intravenously, transdermally, intranasally, rectally, occularly, topically, sublingually, buccally, and the like. Oral administration is generally preferred for treatment of the disorders described herein.

One skilled in the art of preparing Formulations can readily select the proper form and mode of administration depending upon the particular characteristics of the compound selected, the disorder or condition to be treated, the stage of the disorder or condition, and other relevant circumstances. (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and nontoxic in the amounts used.

For the purpose of oral and parenteral therapeutic administration, the compounds f the present invention may be incorporated into a solution or suspension. These preparations typically contain at least 0.1% of a compound of the invention, but may be varied to be between 0.1 and about 90% of the weight thereof. The amount of the compound of Formula I present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the Formula I or its pharmaceutical salt from about 0.1 to about 10% w/v (weight per unit volume).

The compounds of Formula I are agonists of the M-1 muscarinic receptors. Moreover the compounds of Formula I are selective agonists of that particular muscarinic receptor. The compounds of the present invention possess particularly useful properties related to their bioavailability, pharmacokinetics, safety, and efficacy. Muscarinic agonists, including their subtype binding profile, can be identified by the methods that are well known in the art.

In one embodiment, the present invention provides methods of treating disorders associated with muscarinic receptors, comprising: administering to a patient in need thereof an effective amount of a compound of Formula I. Thus, the present invention contemplates the various disorders described to be treated herein and others which can be treated by such agonists as are appreciated by those skilled in the art.

A number of the disorders which can be treated by muscarinic agonists are known according to established and accepted classifications, while others are not. For example, cognition is a complicated and sometimes poorly defined phenomenon. It is, however, widely recognized that cognition includes various "domains." These domains include short term memory, long term memory, working memory, executive function, and attention.

It is understood that the compounds of the present invention are useful for treatment of disorders characterized by a deficit in any of the cognitive domains listed above or in other aspects of cognition. Thus the term "cognitive disorders" is meant to encompass any disorder characterized by a deficit in one or more cognitive domain, including but not limited to short term memory, long term memory, working memory, executive function, and attention.

One cognitive disorder to be treated by the present invention is age-related cognitive decline. This disorder is not well defined in the art, but includes decline in the cognitive domains, particularly the memory and attention domains, which accompany aging. Another cognitive disorder is mild cognitive impairment. Again, this disorder is not well defined in the art, but involves decline in the cognitive domains, and is believed to represent a group of patients the majority of which have incipient Alzheimer's disease. Another cognitive disorder is cognitive impairment associated with schizophrenia. The relationship between cognitive disturbances and other symptoms of schizophrenia is not clearly understood at present. It has been observed that some people experience cognitive problems much before they develop positive symptoms, while others acquire cognitive deterioration after the first episode and with subsequent relapses. Yet another cognitive disorder is chemotherapy-induced cognitive impairment. People who undergo cancer chemotherapy may experience a decline in cognitive function and this decline can be long lasting. Also, a wide variety of insults, including stroke, ischemia, hypoxia, inflammation, infectious processes and cognitive deficits subsequent to cardiac bypass surgery and grafting, stroke, cerebral ischemia, spinal cord trauma, head trauma, perinatal hypoxia, fetal alcohol syndrome, cardiac arrest, and hypoglycemic neuronal damage, vascular dementia, multi-infarct dementia, amylotrophic lateral sclerosis, chemotherapy, and multiple sclerosis can result in cognitive deficits as a sequella which can be treated according to the present invention.

Where the disorders which can be treated by muscarinic agonists are known according to established and accepted classifications, these classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

In particularly preferred embodiments, the present invention provides methods of treating disorders selected from the group consisting of: cognitive disorders (including age-related cognitive disorder, mild cognitive impairment, cognitive impairment associated with schizophrenia, and chemotherapy-induced cognitive impairment), ADHD, mood disorders (including depression, mania, bipolar disorders), psychosis (in particular schizophrenia and schizophreniform disorder), dementia (including Alzheimer's disease, AIDS-induced dementia, vascular dementia, and dementia lacking distinctive histology), Parkinson's disease, Huntington's Chorea, pain (including acute pain and chronic pain), xerostomia (dry mouth), Lewy body disease (including diffuse Lewy body disease), aphasia (including primary aphasia and primary aphasia syndromes), aphasia (including primary aphasia and primary aphasia syndromes), hypotensive syndromes, and chronic colitis (including Crohn's disease), comprising: administering to a patient in need thereof an effective amount of a compound of Formula I. That is, the present invention provides for the use of a compound of Formula I or pharmaceutical composition thereof for the treatment disorders associated with muscarinic receptors.

It is recognized that the terms "treatment" and "treating" are intended to include improvement of the symptomatology associated with each of the disorders associated with muscarinic receptors described herein. Also, it is also recognized that one skilled in the art may affect the disorders by treating a patient presently afflicted with the disorders or by prophylactically treating a patient believed to be susceptible to such disorders with an effective amount of the compound of Formula I. Thus, the terms "treatment" and "treating" are intended to refer to all processes wherein there may be a slowing, interrupting, arresting, controlling, or stopping of the progression of the disorders described herein, but does not necessarily indicate a total elimination of all symptoms, and is intended to include prophylactic treatment of such disorders.

It is understood that the present invention includes adjunctive treatment of the disorders described herein. More specifically, the compounds of Formula I are useful to treat disorders in which a cognitive deficit is one of the symptoms in combination with a wide variety of other therapeutic agents, in particular, in combination with AMPA potentiators; with typical and atypical antipsychotics, including olanzapine; with a variety of agents such as mGluR agonists, with NMDA antagonists, with IL 1-6 inhibitors, with other cholinergics, including cholinesterase inhibitors, such as tacrine and donepezil, and compounds that inhibit amyloid protein processing, including inhibitors of amyloid precursor protein processing and antibodies directed against amyloid proteins; with antidepressants, including SSRIs and SNRIs such as fluoxetine, paroxetine, and venlafaxine; and with anxiolytic agents; etc. It is believed that the combinations above are synergistically beneficial providing efficacy at doses that are a small fraction of those required to produce the same effect with the individual components.

In accordance with the adjunctive treatments described above, the present invention also provides a product containing a compound of Formula I and one or more therapeutic agents selected from the group consisting of AMPA potentiators; typical and atypical antipsychotics, including olanzapine; mGluR agonists; NMDA antagonists; IL 1-6 inhibitors; cholinesterase inhibitors, such as tacrine and donepezil; compounds that inhibit amyloid protein processing, including inhibitors of amyloid precursor protein processing and antibodies directed against amyloid proteins; antidepressants, including SSRIs and SNRIs such as fluoxetine, paroxetine, and venlafaxine; and anxiolytic agents as a combined preparation for simultaneous, separate or sequential administration in the treatment of disorders in which a cognitive deficit is one of the symptoms. In another embodiment the present invention also provides for the use of a compound of Formula I together with one or more therapeutic agents selected from AMPA potentiators; typical and atypical antipsychotics, including olanzapine; mGluR agonists; NMDA antagonists; IL 1-6 inhibitors; cholinesterase inhibitors, such as tacrine and donepezil; compounds that inhibit amyloid protein processing, including inhibitors of amyloid precursor protein processing and antibodies directed against amyloid proteins; antidepressants, including SSRIs and SNRIs such as fluoxetine, paroxetine, and venlafaxine; and anxiolytic agents for the manufacture of a medicament as a combined preparation for simultaneous, separate or sequential administration in the treatment of disorders in which a cognitive deficit is one of the symptoms.

As used herein, the term "simultaneous, separate or sequential administration" means that the two or more therapeutic agents are administered within a time frame which ensures that all of the therapeutic agents will provide some therapeutic activity at a particular point in time. That is to say, the therapeutic activities should at least overlap to some degree although they need not be coterminus.

As used herein, the term "patient" includes a mammal which is afflicted with one or more disorders associated with muscarinic receptors. It is understood that guinea pigs, dogs, cats, rats, mice, horses, cattle, sheep, pigs, and humans are examples of animals within the scope of the meaning of the term.

As used herein, the term "effective amount" of a compound of Formula I refers to an amount, that is, the dosage which is effective in treating the disorders described herein.

An effective amount can be readily determined by the attending diagnostician, as one skilled in the art, by the use of conventional techniques and by observing results obtained under analogous circumstances. In determining an effective amount, the dose of a compound of Formula I, a number of factors are considered by the attending diagnostician, including, but not limited to: the compound of Formula I to be administered; the co-administration of other therapies, if used; the species of mammal; its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of Formula I is expected to vary from about 0.01 milligram per kilogram of body weight per day (mg/kg/day) to about 50 mg/kg/day, and preferable from 0.1 milligram per kilogram of body weight per day (mg/kg/day) to about 20 mg/kg/day. More preferred amounts can be determined by one skilled in the art.

Of the disorders to be treated according to the present invention a number are particularly preferred. Particularly preferred disorders include the treatment of cognitive disorders (particularly mild cognitive impairment and cognitive impairment associated with schizophrenia), Alzheimer's disease, and psychosis, including schizophrenia.

A number of preclinical laboratory animal models have been described for the disorders described herein.

EXAMPLE A

Radial Arm Maze

The delayed non-match to sample task has been used to study the effect of drugs on memory retention (Pussinen, R. and Sirvio, J. *J of Psychopharm* 13: 171-179(1999); Staubli, U., et al. *Proc Natl Acad Sci* 91: 777-781(1994)) in the eight arm radial maze.

Well-trained rats were allowed to retrieve food rewards from four randomLy selected arms of the maze (sampling phase). Some time later, the rats were exposed to eight open arms and were tested for their ability to remember and avoid the arms they had previously entered to obtain food. Re-entry into an arm that was baited during the sampling session was counted as a reference error, whereas entry into the same arm more than once during the retention session was counted as working error. The total (reference+working) number of errors made during the retention test increases with increasing delay periods. For example, young male rats made 0.66 (+0.4) errors at a 1 minute delay, 2 (+0.5) errors at a one hour delay, and 3.95 (+0.2) errors at a seven hour delay (observations of this lab).

Male Sprague-Dawley rats were individually housed and maintained on a 12 h light-dark cycle (lights on at 6 am). The rats were given free access to water and maintained at 85% of their free-feeding weight by supplemental feedings of Purina Lab Chow.

The rats were initially trained to search for food at the end of each of the eight arms. Once the rats had reached the criteria of no more than two errors (i.e. entering the same arm more than once during a session) on three consecutive days, a delay of one minute was imposed between the fourth and the fifth arm choices. This training ensured that the rats were thoroughly familiar with the procedural aspects of the task before any drugs were administered. Once stable performance had been obtained on the delay task (i.e. no more than one error was made on three consecutive days), drug and vehicle tests commenced using a seven hour delay period. A novel set of arms was baited each day for each rat and the maze was thoroughly cleaned during the delay period.

During the sampling session, each rat was placed on the center platform with access to all eight arms of the maze blocked. Four of the eight arms were randomly selected and baited with food. The gates of the baited arms were raised and the rat was allowed five minutes to obtain the food at the end of each of the four arms. As soon as the rat had obtained the food, it was removed, administered vehicle or various doses of compounds, and placed back in its home cage. Seven hours later (retention session), the rat was placed back onto the center platform with access to all eight arms blocked. The four arms that were previously baited during the sampling session, were baited and the gates to all eight arms were raised. The rat was allowed five minutes to obtain the remaining four pieces of food. A n entry into a non-baited arm or a re-entry into a previously visited arm was counted as an error. Significance (p<0.05) was determined using a repeated measure ANOVA followed by a Dunnett's test for comparison with control.

In order to compare test compounds with standards, scopolamine and tacrine were administered s.c. immediately after the sampling phase. The effects of scopolamine, a known amnesic, were tested after a three-hour delay, whereas the effect of tacrine, a cholinesterase inhibitor used in the treatment of Alzheimer's disease was tested after a six-hour delay. Scopolamine disrupted retention after a three-hour delay in a dose-related fashion. Tacrine significantly improved retention after a six-hour delay at 10, but not at 3 mg/kg.

EXAMPLE B

Acquisition in the Radial Maze 8-Arm Radial Maze Acquisition

A prominent early feature of Alzheimer's disease (AD) symptomology is a pronounced deficit in declarative memory (R. W. Parks, R. F. Zec & R. S. Wilson (Eds.), *Neuropsychology of Alzheimer's disease and other dementias*. NY: Oxford University Press pp. 3-80 (1993).

As the disease progresses, other domains of cognition become severely affected as well. Among the brain regions affected early in the progression of Alzheimer's disease is the hippocampus, which is a critical neural substrate for declarative memory. Differences in the pattern of hippocampal neuronal loss in normal aging and Alzheimer's disease. *Lancet*, 344: 769-772(1994). One behavioral test that is often used to assess hippocampal function in animal models is the 8-arm radial maze (Olton D. S. The radial arm maze as a tool in behavioral pharmacology. Physiology & Behavior, 40: 793-797 (1986)).

Lesions or pharmacological blockade of the hippocampus disrupt performance of this task. Moreover, aged animals generally show deficits in this task (Porsolt R. D., Roux S. & Wettstein J. G. Animal models of dementia. Drug Development Research, 35: 214-229(1995)).

In this test of spatial learning and memory, a hungry rat is placed in the center of the maze and allowed to traverse the maze in search of food located at the end of each runway arm. In this version of the maze, the rat learns a win-shift strategy in which a visited arm is not replaced. Therefore, the most efficient foraging strategy is to visit each arm once. The version of the maze also taps into general learning processes as the rat is naive to the maze on day one of the four day experiment.

Upon arrival, male Sprague Dawley®, rats were individually housed in a regular light-cycle colony room and allowed to acclimate for at least 4 days prior to testing. Each rat was reduced to and maintained at 85% of their target body weight throughout the experiment. Proper body weight was maintained by adjusting the allotment of lab chow based on a combination of age and the rat's daily bodyweight reading.

A session began with an individual rat being placed into the hub of the maze and then all guillotine doors were raised, allowing free access to all areas of the maze. A food hopper was located at the end of each of the 8 runway arms and a single food pellet was placed in each food hopper. Each daily session terminated when either all 8 food-hoppers had been visited or when the rat timed out (15 minutes on Day 1: 5 minutes on Days 2-4). The number of arm entries was recorded. Errors were counted as repeat arm entries or failures to visit an arm in the session period. An animal was excluded from the study if it failed to visit at least one arm on Day 1, 2 arms on Day 2, and at least 4 arms on Days 3 & 4.

Each rat was pseudo-randomly assigned to either a vehicle or drug group and received the same treatment throughout the experimental period. Vehicle consisted of 5% acacia within sterile water. Injections were administered subcutaneously 20-30 minutes prior to each daily session.

In this acquisition task, vehicle-treated animals do not consistently show significant acquisition of maze learning as compared to the number of errors committed on Day 1. We have found that in compounds that facilitate acquisition of maze learning, the effects are often not observed until the fourth day of training. Therefore, results consisted of total Day 4 errors across treatment groups.

EXAMPLE C

Functional Mobilization of Intracellular Calcium

CHO cells expressing muscarinic subtypes (M1-M5) are grown as monolayers in DMEM:F-12 (3:1), 10% FBSnz, 20 mM HEPES, 1% pen/strep, 250 µg/mL G418 (GibcoBRL #10131-027). Cells are maintained under 95%/5% $O_2/CO_2$ and passaged every 3-4 days. Cells are plated 24 hours in advance of the assay at a density of 50,000/well and 48 hours in advance at a density of 25,000/well (100 µL/well) in Costar black-walled, clear-bottomed 96 well plates (Costar #3603). Cells are then incubated with minimum essential medium containing the cytoplasmic $Ca^{2+}$ indicator, Fluo-3 (1 mM Fluo mixed 1:1 with 20% pluronic acid, then diluted to 5 µM final concentration in growth and supplemented with 2.5 mM, 50 µL/well) at 37° C. in an environment containing 5% $CO_2$ for 60 minutes. Cells are washed twice with 100 µL/well of wash buffer containing Hanks Balanced Salt Solution (HBSS) without phenol red (1×) (GibcoBRL #14065-056), 20 mM HEPES (Sigma #P8761), and Probenecid (2.5 mM) (100×: 1:100). For the assay, 100 µL is added to each well (100 µL of 2× drug will be added by the FLIPR). Plates are washed three times using a Lab-Systems multidrop and residual buffer is removed. Plates are also blotted on paper towels to remove remaining compound.

Compounds are prepared 2× (100 µL of drug added to 100 µL of assay buffer present in the well) in assay buffer containing 2% DMSO, HBSS without phenol red (1×) (GibcoBRL #14065-056), 20 mM HEPES (Sigma #P8761), and Probenecid (2.5 mM) (100×: 1:100).

The plates were then placed into a FLIPR instrument (fluorometric imaging plate reader system, Molecular Devices, Sunnyvale, Calif.) to monitor cell fluorescence ($\lambda_{EX}$=488 nm, $\lambda_{EM}$=540 nm) before and after the addition of compounds.

The selectivity of the M1 agonists are evaluated by screening across the other muscarinic receptor subtypes (M2, M3, M4 and M5) in a similar manner. Compounds are also screened across a number of protein targets as well as the structurally related G protein-coupled receptor (GPCR) targets to insure selectivity for the M1 receptor.

EXAMPLE D

Functional GTP Binding

Cell Culture: CHO cells transfected with human M1-M5 receptors were grown either in suspension or in monolayer. For suspension cultures cells were grown in roller bottles with constant agitation at 37° C. and 5% $CO_2$ using Dulbecco's modified Eagles medium/F-12 (3:1) culture medium supplemented with 5% fetal bovine serum, 50 µg/mL tobramycin, and 20 mM HEPES. Monolayer cultures were grown in T-225 flasks at 37° C. and 5% CO2 in Dulbecco's modified Eagles medium supplemented with 10% fetal bovine serum and 100,000 U/liter of penicillin/streptomycin. Cells were harvested using trypsin-free dissociation media at 95% confluence and were collected by centrifugation and stored at 80° C. Cells stably expressing human muscarinic receptors were obtained from the National Institutes of Health.

Membrane Preparation: Cell pellets were thawed and resuspended in 20 volumes of 20 mM sodium phosphate buffer, pH 7.4, and were homogenized twice for 30 seconds at high speed using a Tissuemizer. Homogenates were centrifuged at 200 g for 15 minutes at 4° C. The supernatant was removed and reserved on ice. This procedure was repeated twice and the pooled supernatants were then centrifuged at 40,000 g for 45 minutes at 4° C. Membranes were suspended at 5 mg protein/mL and were stored at 80° C. Unless indicated otherwise in the figure legends, membranes from M1, M2, and M4 cells were prepared from cells grown in suspension, whereas those from M3 and M5 cells were from cells grown in monolayer. Receptor densities (pmol mg1 membrane protein) were 9.3, 0.7, 0.6, 0.9, and 4.8 for M1-M5 receptors, respectively.

Striatal tissue from male Sprague-Dawley rats was homogenized by hand in 10 volumes of 10 mM HEPES and 1 mM EGTA, pH 7.4, containing Complete protease inhibitor cocktail, 1 mM dithiothreitol, and 10% sucrose. The homogenate was diluted 6-fold and centrifuged at 1000 g for 10 minutes at 4° C. The supernatant was saved and the pellet rehomogenized and centrifuged as above. The combined supernatants were centrifuged at 11,000 g for 20 minutes. The resulting pellet was homogenized in 40 volumes of 10 mM HEPES and 1 mM EGTA, pH 7.4, containing 1 mM dithiothreitol and 1 mM $MgCl_2$, and was centrifuged at 27,000 g for 20 minutes. The resulting pellet was suspended in the same buffer at a protein concentration of 1.5 mg/mL and aliquots were frozen and stored at 80° C.

GTP$\gamma^{35}$S Binding: Assays were run in 20 mM HEPES, 100 mM NaCl, and 5 mM $MgCl_2$ at pH 7.4 in a final volume of 200 µl in 96-well Costar plates at 25° C. One hundred microliters of membrane preparation (25 µg protein per well for cell membranes and 9-15 µg per well for brain membranes) containing the appropriate concentration of GDP was added followed by addition of 50 µl of buffer±agonists and antagonists being tested followed by 50 µl of GTP$\gamma^{35}$S to provide a final concentration in the assay of 200 pM for CHO membranes and 500 pM for brain membranes. For CHO membranes, 0.1 µM GDP was used for M1, M3, and M5 receptor assays, whereas 1 µM GDP was used for M2 and M4 assays. For brain membranes, 0.1 µM GDP was used in assays carried out with anti-G$\alpha$q/11, whereas 50 µM GDP was used for assays using anti-G$\alpha$i(1-3) and anti-G$\alpha$o. CHO cell membranes were incubated for 30 minutes at 25° C. with agonists and antagonists followed by addition of GTP$\gamma^{35}$S and incubation for an additional 30 minutes. Brain membranes were incubated for 20 minutes at 25° C. with agonists and antagonists followed by addition of GTP$\gamma^{35}$S and incubation for an additional 60 minutes. Preincubation was employed to ensure that agonists and antagonists were at equilibrium during the labeling period.

To determine total membrane binding, 50 µL of suspended wheat germ agglutinin (WGA)-coated SPA beads was added. After 15 minutes, plates were centrifuged at 1000 g for 15 minutes and radioactivity was determined using a Wallac plate counter. For determining binding to specific G proteins, $^{35}$S-labeled membranes were solubilized for 30 minutes with 0.27% Nonidet P-40 (20 µL/well of a solution containing 1.5 mL of 10% Nonidet P-40 for every 3.5 mL assay buffer) followed by addition of desired antibody (10 µl/well) to provide a final dilution of 1/400 to 1/100 and incubation for an additional 60 minutes. Fifty microliters of suspended anti-IgG-coated SPA beads was added per well, plates were incubated for 3 hours, and then were centrifuged and radioactivity determined as above. Each bottle of WGA-coated SPA beads was suspended in 10 mL of assay buffer and each bottle of anti-IgG-coated SPA beads was suspended in 20 mL of assay buffer. Protein was determined using the bicinchoninic acid assay.

Materials: $^{35}$S-GTPγS (1000-1200 Ci/mmol), anti-rabbit-IgG and anti-mouse-IgG-coated SPA beads, and WGA-coated SPA beads were obtained from Amersham (Arlington Heights, Ill.). Rabbit anti-Gαq/11 and rabbit anti-Gαi(1-3) were from Santa Cruz Biotechnologies (Santa Cruz, Calif.). Mouse monoclonal anti-Gαo was from Chemicon (Temecula, Calif.). Oxotremorine M and pirenzepine were from Research Biochemicals Inc. (Natick, Mass.). 11-{[2-((Diethylamino)methyl)-1-piperidinyl]acetyl}-5,11-dihydro-6H-pyrido[2,3b][1,4]benzodiazepin-6-one (AFDX 116) was synthesized at Eli Lilly. Complete protease inhibitor cocktail and 10% Nonidet P-40 were from Boehringer Mannheim (Indianapolis, Ind.).

The selectivity of the M1 agonists are evaluated by screening across the other muscarinic receptor subtypes (M2, M3, M4 and M5). Compounds are also screened across a number of protein targets as well as the structurally related G protein-coupled receptor (GPCR) targets to insure selectivity for the M1 receptor.

What is claimed is:

1. A compound of the Formula

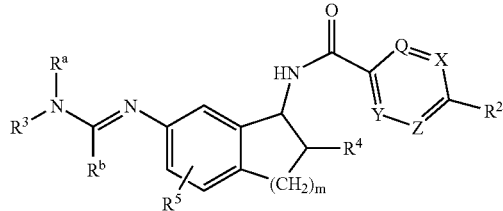

wherein

Q, X, Y, and Z are independently selected from the group consisting of $CR^1$ and N, provided that no more than two of Q, X, Y, and Z are N and at least two of Q, X, Y, and Z are CH; or Y is CH, Z is CH, and the moiety "Q=X" represents "S" to form a thiophene ring;

$R^1$ is independently at each occurrence selected from the group consisting of hydrogen, halogen, $C_1$-$C_4$ alkoxy, and $C_1$-$C_4$ alkyl;

$R^2$ is selected from the group consisting of halogen; $C_1$-$C_4$ alkoxy; $C_1$-$C_4$ alkyl; $C_3$-$C_8$ cycloalkyl; cyano; trifluoromethyl; pyridinyl optionally substituted with one to two substituents independently selected from the group consisting of halogen, $C_1$-$C_4$ alkoxy, and $C_1$-$C_4$ alkyl; thienyl optionally substituted with one substituent selected from the group consisting of halogen, $C_1$-$C_4$ alkoxy, and $C_1$-$C_4$ alkyl; phenyl optionally substituted with from one to three substituents independently selected from the group consisting of halogen, $C_1$-$C_4$ alkoxy, $C_1$-$C_4$ alkyl, trifluoromethyl, and cyano; and pyrrolyl optionally substituted with one to two substituents independently selected from the group consisting of halogen, $C_1$-$C_4$ alkoxy, and $C_1$-$C_4$ alkyl;

$R^3$ is a radical of the formula (Z)-(Y)—(X)— wherein

X is selected from the group consisting of

and a straight-chain $C_1$-$C_4$ alkandiyl optionally substituted with methyl, geminal dimethyl, or phenyl;

Y is selected from the group consisting of O and S; and

Z is selected from the group consisting of $C_1$-$C_6$ alkyl; $C_3$-$C_8$ cycloalkyl optionally substituted with one to three substituents independently selected from the group consisting of halogen, $C_1$-$C_4$ alkoxy, C 1-$C_4$ alkyl, trifluoromethyl, cyano, and nitro; phenyl optionally substituted with one to three substituents independently selected from the group consisting of halogen, $C_1$-$C_4$ alkoxy, $C_1$-$C_4$ alkyl, trifluoromethyl, cyano, and nitro; naphthyl optionally substituted with one to three substituents independently selected from the group consisting of halogen, $C_1$-$C_4$ alkoxy, $C_1$-$C_4$ alkyl, trifluoromethyl, cyano, and nitro; heteroaryl optionally substituted with one or two substituents independently selected from the group consisting of halogen, $C_1$-$C_4$ alkoxy, and $C_1$-$C_4$ alkyl; and heterocycle optionally substituted with one or two substituents independently selected from the group consisting of halogen, $C_1$-$C_4$ alkoxy, and $C_1$-$C_4$ alkyl;

$R^a$ is selected from the group consisting of hydrogen and methyl;

$R^4$ is selected from the group consisting of hydrogen, hydroxy, and fluoro;

$R^5$ is selected from the group consisting of hydrogen, halogen, $C_1$-$C_4$ alkoxy, and $C_1$-$C_4$ alkyl;

$R^b$ is selected from the group consisting of hydrogen, methyl, and ethyl; and m is one or two;

or pharmaceutically acceptable addition salts thereof.

2. A compound of claim 1 wherein $R^5$ is hydrogen, $R^4$ is hydroxy, m is one, and which has the trans stereochemistry at the 1- and 2-position shown below:

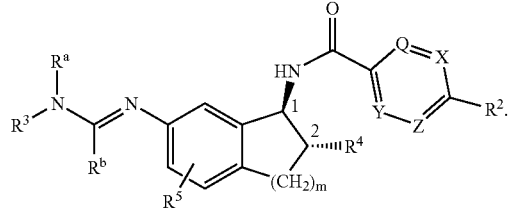

3. A compound according to claim 1 wherein Q, X, Y, and Z are each CH.

4. A compound according to claim 2 wherein Q, X, Y, and Z are each CH.

5. A compound according to claim 1 wherein one of Q, X, Y, and Z is CF and the others are CH.

6. A compound according to claim 2 wherein one of Q, X, Y, and Z is CF and the others are CH.

7. A compound according to claim 1 wherein Q is CF, and X, Y, and Z are each CH.

8. A compound according to claim 1 wherein $R^2$ is phenyl optionally substituted with from one to three substituents independently selected from the group consisting of halogen, $C_1$-$C_4$ alkoxy, $C_1$-$C_4$ alkyl, trifluoromethyl, and cyano.

9. A compound according to claim 1 wherein $R^2$ is phenyl.

10. A pharmaceutical composition comprising a compound of claim 1 and a pharmaceutically acceptable diluent.

11. A method of treating Alzheimer's disease, comprising: administering to a patient in need thereof an effective amount of a compound of claim 1.

12. A method of treating schizophrenia, comprising: administering to a patient in need thereof an effective amount of a compound of claim 1.

* * * * *